(12) United States Patent
Harwig et al.

(10) Patent No.: US 6,909,840 B2
(45) Date of Patent: Jun. 21, 2005

(54) LOCALIZED SURFACE VOLATILIZATION

(75) Inventors: Jeffrey L. Harwig, New Berlin, WI (US); Brian E. Healy, Hartland, WI (US); James F. Kimball, Hales Corners, WI (US); Stephen B. Leonard, Franksville, WI (US); Maude Christian Meier, Racine, WI (US); Ralph W. Oakeson, Boonton, NJ (US)

(73) Assignee: S. C. Johnson & Son, Inc., Racine, WI (US)

(*) Notice: Subject to any disclaimer, the term of this patent is extended or adjusted under 35 U.S.C. 154(b) by 46 days.

(21) Appl. No.: 10/455,665

(22) Filed: Jun. 5, 2003

(65) Prior Publication Data

US 2004/0035409 A1 Feb. 26, 2004

Related U.S. Application Data

(60) Provisional application No. 60/386,998, filed on Jun. 6, 2002.

(51) Int. Cl.$^7$ .................................................. F24F 6/08
(52) U.S. Cl. ......................................... 392/405; 392/395
(58) Field of Search ................................ 392/386, 390, 392/391, 392, 394, 395, 405, 406; 43/129, 130; 122/366, 367.1, 367.2; 239/44, 45; 219/543, 544

(56) References Cited

U.S. PATENT DOCUMENTS

| | | | |
|---|---|---|---|
| 616,049 A | 12/1898 | Archer | |
| 2,041,219 A | 5/1936 | Wade | 21/18 |
| 2,140,516 A | 12/1938 | Cowan | 219/40 |
| 2,606,095 A | 8/1952 | Bateman et al. | |
| 3,110,256 A | 11/1963 | Barber et al. | 102/7.2 |
| 3,623,260 A | 11/1971 | Konle | 43/129 |
| 3,778,924 A | 12/1973 | Okui | 43/129 |
| 3,931,492 A * | 1/1976 | Takano et al. | 347/203 |
| 3,993,582 A | 11/1976 | Curtis | 252/359 A |
| 4,163,038 A | 7/1979 | Nishimura et al. | 422/36 |
| 4,228,124 A | 10/1980 | Kashihara et al. | 422/36 |
| 4,465,458 A * | 8/1984 | Nishino et al. | 431/208 |
| 4,693,890 A | 9/1987 | Wilson et al. | 424/78 |
| 4,696,676 A | 9/1987 | Wilson et al. | 44/7.5 |
| 4,756,118 A | 7/1988 | Evans | 43/132.1 |
| 4,777,032 A | 10/1988 | Barruet et al. | 424/42 |
| 4,777,345 A * | 10/1988 | Manchester | 392/390 |
| 4,780,286 A | 10/1988 | Parent et al. | 422/125 |
| 4,839,144 A | 6/1989 | Martin | 422/305 |
| 4,844,050 A | 7/1989 | Hautmann et al. | 126/43 |
| 5,094,025 A | 3/1992 | Daniels | 43/1 |
| 5,234,162 A | 8/1993 | Sullivan | 239/56 |
| 5,387,418 A | 2/1995 | Marin et al. | 424/409 |
| 5,458,882 A | 10/1995 | Marin et al. | 424/411 |

(Continued)

FOREIGN PATENT DOCUMENTS

| | | | |
|---|---|---|---|
| DE | 3515460 A1 | 10/1985 | A01M/1/00 |
| EP | 0470088 B1 | 6/1994 | A01M/13/00 |
| EP | 0362397 B1 | 7/1994 | A01M/1/20 |
| EP | 0911041 A3 | 9/2000 | A61L/9/03 |
| GB | 1123922 | 8/1968 | A61I/9/02 |
| GB | 1123923 | 8/1968 | A31I/9/02 |
| WO | WO90/13359 | 11/1990 | B01J/7/00 |
| WO | WO97/28830 | 8/1997 | A61L/9/03 |
| WO | WO01/93674 A2 | 12/2001 | A01M/1/20 |

*Primary Examiner*—Sang Y. Paik

(57) ABSTRACT

The present invention relates to an apparatus and method for rapid flash-like volatilization of high and low vapor pressure components from liquid or solid emanators which is in contact with a point or localized heat source. Vaporization is promoted by a geometrically small electrically resistive heating element with variable activation for pulsed or cyclic heating of an emanating surface containing the volatile components. The apparatus is primarily directed towards the treatment of residential air for fragrancing, odor elimination, treatment of insects or pests, air sanitization, air and surface antibacterial or antimicrobial treatment, or other ambient air or surface modification by way of gas or vapor distribution.

55 Claims, 13 Drawing Sheets

U.S. PATENT DOCUMENTS

| | | | |
|---|---|---|---|
| 5,484,086 A | 1/1996 | Pu | 222/187 |
| 5,644,866 A | 7/1997 | Katsuda | 43/129 |
| 5,647,052 A | 7/1997 | Patel et al. | 392/390 |
| 5,692,095 A | 11/1997 | Young | 392/395 |
| 5,903,710 A | 5/1999 | Wefler et al. | 392/392 |
| 5,945,094 A | 8/1999 | Martin et al. | 424/76.1 |
| 5,971,367 A | 10/1999 | Skelding | 261/39.1 |
| 5,976,503 A | 11/1999 | Martin et al. | 424/43 |
| 5,991,507 A | 11/1999 | Bencsits | 392/395 |
| 6,123,935 A | 9/2000 | Wefler et al. | 424/76.1 |
| 6,242,722 B1 * | 6/2001 | Provancha et al. | 219/543 |
| 6,248,257 B1 | 6/2001 | Bell et al. | 252/70 |
| 6,278,840 B1 * | 8/2001 | Basaganas Millan | 392/390 |
| 6,289,889 B1 | 9/2001 | Bell et al. | 126/263.07 |
| 6,392,549 B1 | 5/2002 | Wu | 340/573.2 |
| 6,659,301 B2 * | 12/2003 | Fellows et al. | 215/400 |
| 2001/0053283 A1 | 12/2001 | Levine et al. | 392/395 |
| 2002/0005437 A1 | 1/2002 | Ketcha et al. | 239/13 |

* cited by examiner

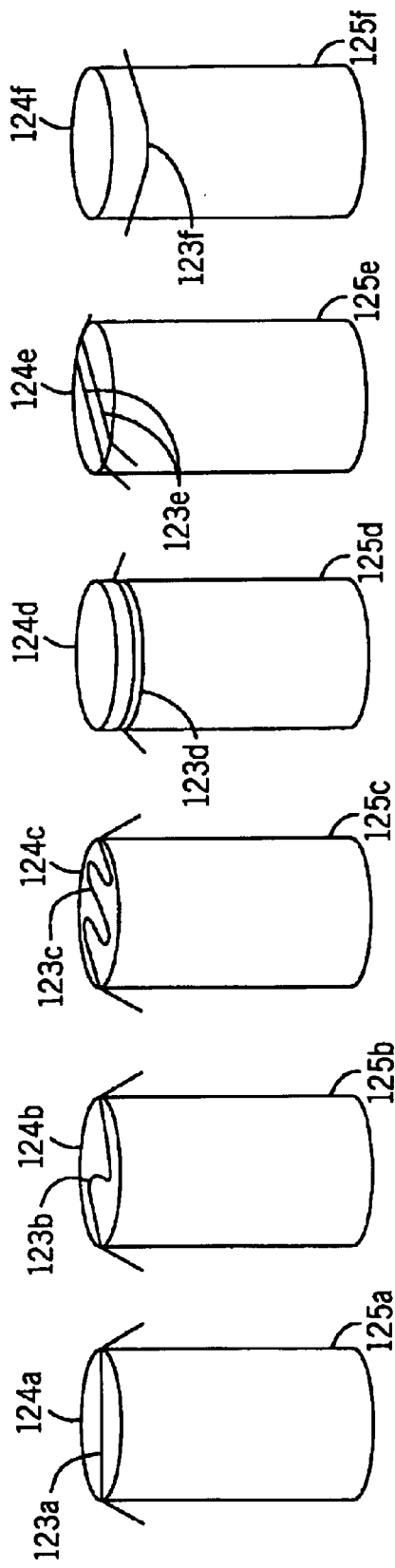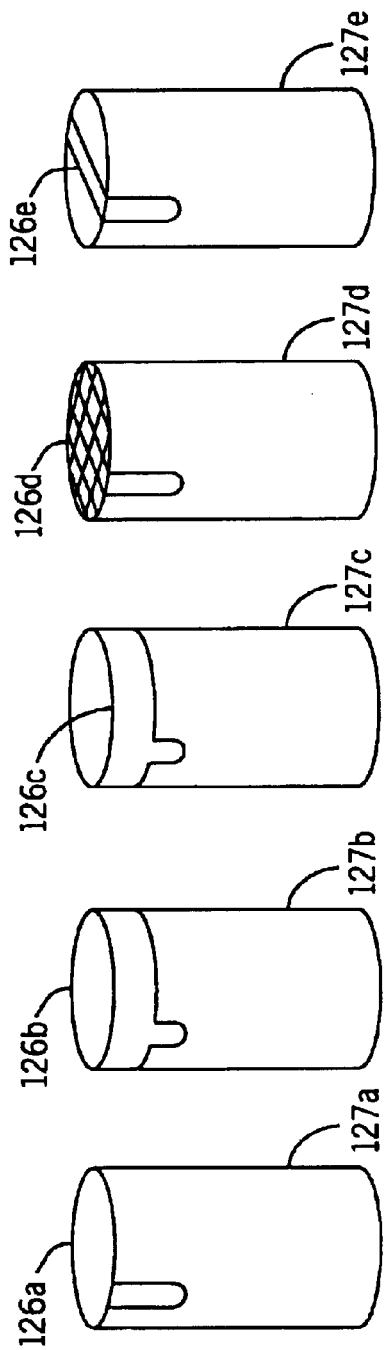

LOCALIZED SURFACE VOLATILIZATION

CROSS-REFERENCE TO RELATED APPLICATION

This application is based on and claims priority from provisional patent Application No. 60/386,998 filed on Jun. 6, 2002.

BACKGROUND OF THE INVENTION

The present invention relates to an apparatus and method for rapid flash-like volatilization of high and low vapor pressure components from liquid or solid emanators which is in contact with a point or localized heat source. Vaporization is promoted by a geometrically small electrically resistive heater material with variable activation for pulsed or cyclic heating of the emanating surface containing the volatile components.

The field of the invention is primarily directed towards the treatment of residential air for fragrancing, odor elimination, treatment for insects or pests, air sanitization, air and surface antibacterial or antimicrobial treatment, or other ambient air or surface modification by way of gas or vapor distribution. Applications include portable, e.g. wearable or carried on an individual's belt, fixed for localized treatment, e.g. covering a relatively small area, or fixed for space treatment, e.g. covering an entire room of a house or building. Other fields of use could include commercial and other public environments requiring air or surface modification by gaseous treatment.

Air modification and treatment has been a part of dwelling, recreational, work, and other indoor and localized outdoor environment aesthetics and functionality throughout history. An inherent problem has been that aesthetic or functional volatiles with sufficiently high vapor pressure to adequately treat the environment by unaided means are limited in number and their treatment benefit. As a result there has been a long history of the use of heat to assist in the vaporization of higher molecular weight and lower vapor pressure compounds.

The use of heat increased the range of aesthetic and functional compounds that can be used for air quality management. Some of the first would have used flame (candle systems, stovetops, etc.). Although effective, and continues to be used today, heat from a flame can be difficult to use because the magnitude of heat is difficult to regulate, and a flame typically has wide fluctuations of temperature ranges. Other problems include the affect on larger surfaces, i.e. unintended areas may be raised in temperature, the soot from a flame can blacken components, a flame can give off an unpleasant odor, the solution to be volatized can be rapidly degraded, and there is little adjustment. As a result, many materials are eliminated for use with flame systems.

In addition to flame based systems, there have emerged chemical heat emanation enhancers. Many well-known and simple chemistries are available as described in U.S. Pat. Nos. 6,248,257 and 6,289,889, and include calcium oxides, aluminum copper sulfate, potassium chlorate, calcium sulfate, iron oxide, acids and bases, and others. Chemical heat sources suffer from inadequate means to closely control temperature, ability to stop the reaction, and many have pre- or post-reaction aggressive components.

Another generation of delivery methods includes devices such as compressed gases or aerosols, which propel minute droplets creating great aggregate surface area for volatilization of a liquid composition into the air. These systems work well for instant and situational applications, but have yet to be as viable for continuous air treatment. A simple set of technologies to address this interest area have been dispensing devices with open or semi-closed supported gelatinous, fibrous, or other material of absorbed or adsorbed actives and enhancers that promotes passive emanation by increased surface area. The needed large surfaces cause these products to be large, heavy, and have unsightly use features as the gels shrink, structures are exposed, surfaces soil, etc.

Other passive metering systems that have emerged and have been used include semipermeable membranes, wicks, capillaries, porous materials or other fluidic transport and emanating surfaces. Other products such as deodorant and sublimation blocks are also used for dispensing air-treating vapors into the atmosphere by evaporation. The performance of these systems vary widely, and although there are hybrid systems of new materials and designs that promote vaporization by passive methods, they can suffer from the same drawbacks listed with gel and fibrous systems, and they generally lack optimal performance attributes.

There has been increasing use of electrified systems to promote enhanced volatilization, through the use of heat, air movement, electromechanical aerosolizers, or other methods or combinations. Heat and/or airflow have been combined with many of the passive air modification methods mentioned above. Airflow systems are marginally better than passive systems and continue to require somewhat larger emanating surfaces to achieve enhancement. The added system energy has provided for actives with better effectiveness, and depending upon the complexity of these devices, more optimal delivery performance. Although these systems are generally successful they leave important performance characteristics unaddressed.

SUMMARY OF THE INVENTION

The present invention provides an apparatus and a heating method using a localized heater with pulsed activation that can be incorporated for use in domestic or commercial, indoor or outdoor, fixed or portable applications. The apparatus includes an electro-resistive heating element such as a wire, thin film, or thick film resistive heater touching or affixed to an emanating surface from which a volatile compound can be vaporized by heat generated from pulsed electrical input. Preferably, the heater includes a Nicrome wire that contacts a wick which is heated to vaporize an active on the surface of the wick into the surrounding air. Heating is preferably accomplished using alkaline or rechargeable batteries, and tabletop as well as portable, wearable devices are contemplated. The localized heater and pulsed cycling work jointly to create rapid heating and cooling, limited thermal conductivity away from the local heat zone, meter effluent release by the magnitude, duration, and frequency of electrical cycles, and impart less thermal damage to the effluent. The heater is a component of technology that can be integrated with other methods of emanation enhancement, such as moving air, as well as visual or audible stimulus.

The present invention addresses many of the unmet performance attributes of prior devices. One such is the need for portability. Passive devices are portable, but generally ineffective. Powered devices are more effective but restricted to being relatively close to electrical power outlets, and battery powered devices are limited to the use of less energy consuming emanation enhancement technologies such as fans, as resistive heaters rapidly consumes available battery energy. The inability to use heat, again substantially limits the actives that can be effectively used with the unit. All current devices also remain relatively unresponsive to the functional or aesthetic demands and preferences for which the product is intended, such as full space treatment, variable treatment strength, alteration of systems to different chemistries, etc. The present invention overcomes these issues by addressing the important performance issue of using an efficient resistive heater and minimizing the size of the heater to only the very small area needed to achieve desired emanation.

It is a further advantage of this invention to provide volatilization enhancement that improves air treatment performance. Specifically, this involves the use of pulsed heating of a thin film low thermal mass heater that rapidly heats and cools. This permits the heater to be used for metering the amount of active emanated by the magnitude, duration, and frequency of heating. Varying these parameters allows for adjustability to treat environments that change in size, air treatment need, personal preference, and characteristics of different actives and solutions. Such features have not been available with constant heat systems whether the source is a flame, electrical resistive heat, chemical reaction, etc. Air movement systems are also usually fixed in their airflow, and even with those that do modulate, the use of airflow can be limiting for lower vapor pressure component usage.

This invention also provides the advantage of using localized and pulsed heating to reduce changes in emanation effluent composition. Typical use of heat for emanation enhancement has placed the solution at constant and elevated temperature. The result is that not only is the relatively large heater and immediate area of the emanating surface brought to elevated temperature, but quickly the device, the matrix or container and its contents are also elevated in temperature. This results in not only increased general emanation, but the constant application of heat accelerates concentration change as the high vapor pressure constituents will emanate more rapidly than the lower vapor pressure constituents. This will cause a continuous change in the solution concentration and create a change in the desired composition of the effluent.

The constant application of heat also places constituents at higher temperature and molecular energy that accelerates the kinetics toward molecular degradation. Using carbon based compounds as an example, with the most common and weaker of them being C—C, C—H, C—N, and C—O, all having less than 100 kcal/mole bond strength. With an average bond strength being about 80 kcal/mole, these bonds would be supplied with sufficient energy for degradation at high constant temperatures. Considering Joule's Law a relevant value of the amount of heat produced by a conductor from the flow of current can be obtained. That is, $H=KI^2Rt=KtP$, where: H=heat (cal), K=constant of proportionality and is valued at 0.2390 (cal/j), I=current (A), R=resistance of the conductor ($\Omega$), and t=time (s), and P=power (watt=j/s). Typical values for the localized and pulsed resistive heater can range from 0.25–3 seconds pulsed on-time, 0.2–25 ohms, and 0.2–1 amperes per cycle. At the extremes this represents a heat value H<<80 kcal/mole for the short pulse cycles. However, by constant heating it is just a few hours before energies have been input into the system equivalent to those needed for degradation of chemical bonds. This energy is dissipated throughout the solution, its container, the wick, and other structural components. The constant application of heat significantly contributes to accelerating degradation kinetics. These undesirable results can be substantially minimized or eliminated by the combined effect of both cyclic and localized heating.

Localized heating implies the use of reduced emanation surfaces. This is possible because the pulsed heating can vary in magnitude, duration, and frequency to get equivalent emanation amounts needed from a smaller area. The benefit of a smaller area is less surface for low temperature release of the higher vapor pressure components of a product, resulting in more uniform product over time. Also because of the nature of pulsed heating, the emanator and effluent in the vicinity of the heater is usually not in a thermal environment and the effluent is not subjected to long and continuous higher energy environments. Also, because of the discontinuous application of heat there is limited heat transfer at proximal or further distances from the heater. These conditions reduce possible effluent degradation and increase effluent stability over time.

When heat is applied with a localized cyclic heater, it can be controlled and directed for optimal vaporization. Vapor pressure of a liquid occurs because at any temperature there is a distribution of kinetic energy held by the molecules in solution. Those with higher energies sufficient to escape the surface of the liquid are vaporized and an equilibrium of vaporization with condensation is reached at the given conditions. By adding heat into the liquid the distribution of molecules with sufficient escape energy increases, rising the rate of vaporization and vapor pressure. By recognizing that vaporization is a surface event, and it is singly the process of vaporizing of the liquid that is desired, then surface heating provides the most efficient method to transfer heat to surface molecules and minimizing the transfer of heat to bulk liquid and degradation processes. Such a mechanism of vaporization can increase energy efficiency of the system. Submerging a heater results in equivalent energy transfer, but the energy within the liquid is subsequently dissipated. At the liquid interface, high energy molecules are allowed to escape or diffuse short distances to the surface and then escape as a vapor. Within the liquid high energy molecules transfer their energy by collision to other molecules before escaping, resulting in bulk liquid heating. At temperatures below boiling where vapors do not accumulate into bubbles that can protect the vapor and rise quickly to the surface, many high energy molecules do not reach the surface to escape, thus lowering the efficiency of vaporization for small energy inputs. Consequently, the depth of the surface can extend beyond the distance of a few molecules that are needed for molecular properties at the liquid interface to transition to molecular bulk liquid properties. The nature of the viscosity, intermolecular interaction, and other characteristics of the solution, its various constituents, and their specific ability to reach the surface because of their molecular size, functionality, structure, degree of intermolecular interaction, and other considerations will determine the effective surface thickness that will allow for the rapid vaporization of such constituents without significant loss to bulk heating. A practical consideration for efficiency is that the majority of vaporized molecules escape the surface to include those vaporizing under the heater or opposite the surface, if such condition exists, and which would create longer pathways for escape. A practical definition of this surface thickness is considered 300 $\mu$m and more preferably 100 $\mu$m with an understanding that thermal lines from a heater are often confined to one diameter or thickness away from the heater and this represents the zone of heating by minimal conductive processes. Surface heating in central to the design of a portable, low energy heat source. Cyclic heating allows for the use of broad temperature ranges with minimal effluent concentration and molecular changes.

Localized and cyclic heating that can vary in its magnitude, duration, and frequency parallels the proportional relationship of increased temperature with increased vaporization. As a result, optimal evaporation can occur regardless of the chemical and physical characteristics of the substance being evaporated. This relationship follows the condensed phase-vapor equilibrium of log $P=-\Delta H/RT+C$, where P=pressure, $\Delta H$=system interaction enthalpy, R=gas constant, T=temperature (K), and C=constant. A log P is plotted against 1/T and shows increasing vapor pressure with increasing temperature between a condensed phase and a vapor phase. The input of low heat for longer cyclic duration or the input of high heat for short duration and frequency of these cycles each achieve similar amounts of vaporized liquid. Localized low mass heaters allow for rapid heating to temperatures, preferably near, but below boiling points. This is not a necessity as multicomponent mixtures for many solutions and even complex mixtures for fragrance solutions will have wide ranges in boiling points of the constituents. It is more important that a rapid heating and then cooling cycle occur that promotes uniform evaporation of all components through a rapid or flash-like vaporization. This mechanism provides for rapid treatment of a space while preserving the concentration and molecular stability of the solution. Lower temperatures and longer on-time cycles can be used to achieve initial treatment or maintenance of the vapor in the space, but then the application becomes more reminiscent of current systems that suffer from extended heating. It is preferred that maintenance be achieved by rapid heating and then cooling, but with less frequency. Thus continuing to preserve solution concentration and molecular stability. As a result, the magnitude and duration of the heating cycle can meter the rate over time, or quantity per cycle vaporized using localized cyclic heating.

Typically, the addition of heat in the localized cyclic heater preferentially creates rapid heat for flash-like evaporation. Doing so limits the flow or flux of heat distantly from the heat source, as governed by Fourier's Law, $q=-kA(MT/Mx)$, where q=heat transfer, k=thermal conductivity of the material, A=unit area of transfer, (MT/Mx)=the temperature gradient. Thermal conductivities of $3.3\times10^{-4}$ cal/(sec)(cm$^2$)(° C./cm) for light hydrocarbon oils representative of organic liquids, aqueous solutions of $4.3\times10^{-5}$ cal (gm)/(sec)(cm$^2$)(° C.), and $60.3\times10^{-6}$ cal/(sec)(cm$^2$)(° C./cm) for air. These values indicate that the thermal conductivity for air creates an insulative barrier that does not permit effective thermal transfer from noncontact heat sources which are common in many applications. This invention takes advantage of reduced heat transfer by rapid contact heating, limited cyclic timing, and use of inherent low thermal conductivity of common light hydrocarbon or aqueous solutions of $10^{-4}$–$10^{-5}$ thermal conductivity to provide an optimal volitalizer of effluents for air modification with limited energy use and improved product stability.

In addition, localized and pulsed heating creates the opportunity for greater portability of a product employing these technologies. Localized heating implies that heat is confined to a specific area. This can be accomplished by limiting the magnitude, duration, and frequency of heating and taking advantage of material properties for limiting undesired thermal transfer. It also suggests that the geometric size and shape of the heater locally confines the influence of heat. Another less obvious aspect of localized heating is the specific composition, performance, spatial positioning, dimension, and design of the heater to provide focused heating. A proper selection of these elements provides for localized heating. The smaller dimension provides for greater design flexibility into products where size becomes a consideration. Simplicity of the heater allows for broader use and even multiple use within the same application. Incorporating the above considerations as well as efficient power usage criteria, a heater can be specified that allows for conventional or battery power with desirable battery life and heater performance characteristics. Pulsing the heater is integral to permitting extended use of battery power or efficient use of wall power, and safety considerations as the heater circuit is usually not closed and drawing power.

A further advantage of this technology is the simplicity that enables previously impractical applications of multiple and independent heaters because of heater size. For example, control of the heater may be analog or digital or the heater may even be remotely actuatable. This has not been previously available because of the lack of thermal responsiveness in cooling and heating that would cause effluents to emanate simultaneously, unless desired, etc. The simplicity of electrical heating coupled with the benefits of localized and pulsed heating allow for the incorporation of multiple emanators. Such an embodiment creates products that deliver multiple fragrances to overcome human adaptation, which is manifest by the inability to detect the presence of the fragrance over time. Changing fragrances by pulsing different emanators from time to time, any adaptation is mitigated as the physiological changes associated with the environmental change are then detected. An extension of multiple emanators could include also include a combination of fragrances, odor eliminators, insect repellents, insecticides, fungicides, antibacterials, etc.

Central to the volatilization and energy use efficiency of the localized and pulsed heater is its spatial location to the emanator. Preferably the heater is in close proximity and even touching or mounted to the surface of the emanator. Because of the need for only a geometrically small heater, the emanator also need not be large and preferably would be small. This close association is not preferred in the fact that the emanator matrix will absorb heat that is then unavailable for vaporization, but such a close position to the release matrix also places the heater in close proximity to the effluent. Because of the insulative properties of many media such as air, ceramic, etc. it is advantageous to have the heater in contact with the effluent to facilitate the most efficient thermal transfer and volatilization. In connection with this, the heater becomes more supported or affixed to the matrix, becomes more robust, and maintains more consistent spatial proximity to the effluent.

Yet an additional advantage of this invention is the use of an affixed heater to the effluent refill. The refill assembly may thus include not only a reservoir containing a composition having a volatile active, and a wick having an emanating surface for the active, but also the heater element itself. The incorporation of these elements provides for the consistency and robustness suggested above with the heater. A heater affixed to a refill provides the spatial relationship most effective for volatilization of surface liquid. It also provides for a renewed heater with each refill purchase, such that there is reduced risk of matrix fouling near the heater or fouling and reduced efficiency in thermal transfer from the heater to the effluent. It also provides a proprietary interface between refill and the support system to ensure that the safety, performance, specifically designed effluents, and other factors are preserved by using appropriate refills.

BRIEF DESCRIPTION OF THE DRAWINGS

FIG. 1 is a perspective view of a localized cyclic heater in accordance with the present invention using NiCr resistive wire with multiple emanators;

FIG. 2 is a perspective view of the heater in FIG. 1 with its cover off exposing selected components in the circuitry and user interface;

FIG. 3 is a schematic illustration of electronic circuitry for the heater of FIGS. 1 and 2 to provide for cyclic localized heating of the multiple emanators;

FIGS. 4a–4f schematically illustrate various resistive wire heater designs to change the thermal characteristic of the heater;

FIGS. 5a–5e schematically illustrate various thin film resistive heater designs to change the thermal characteristic of the heater;

Figure 11:
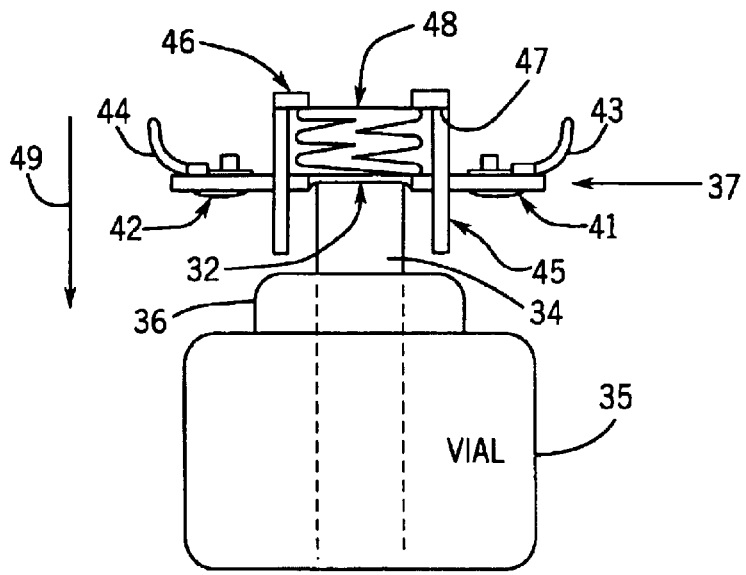
Figure 12:
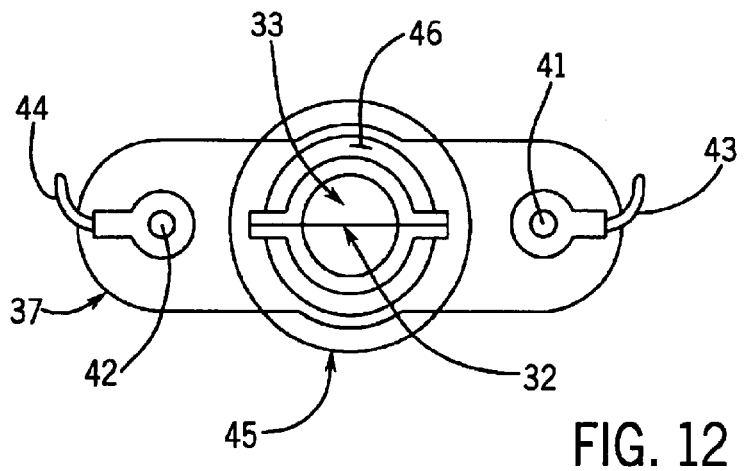
Figure 13:
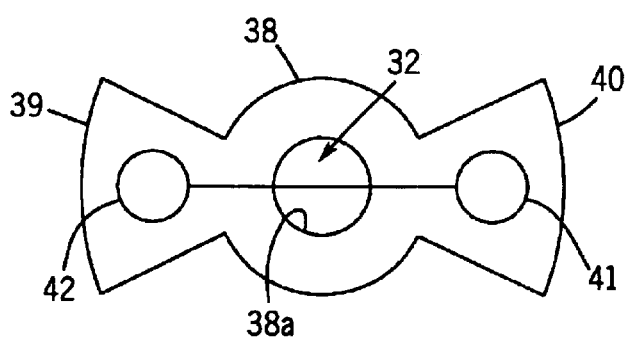
Figure 14:
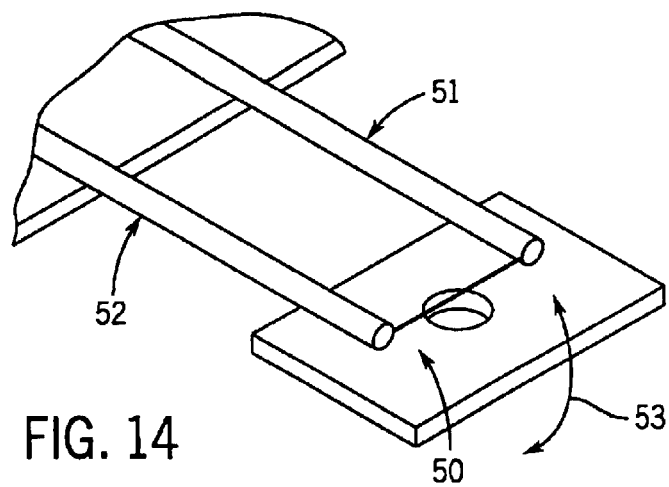
Figure 15:
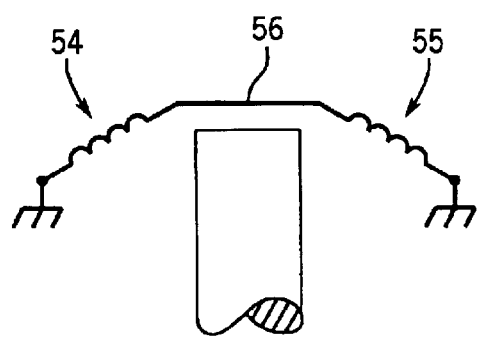
Figure 16:
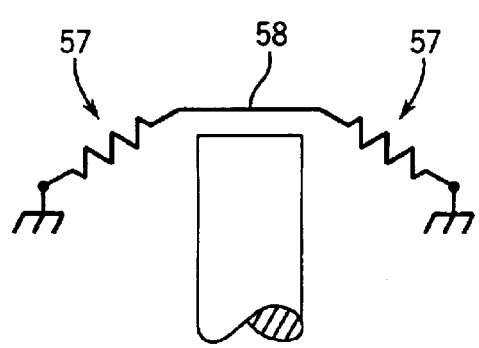
Figure 17:
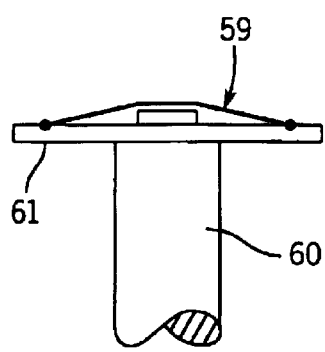
Figure 18:
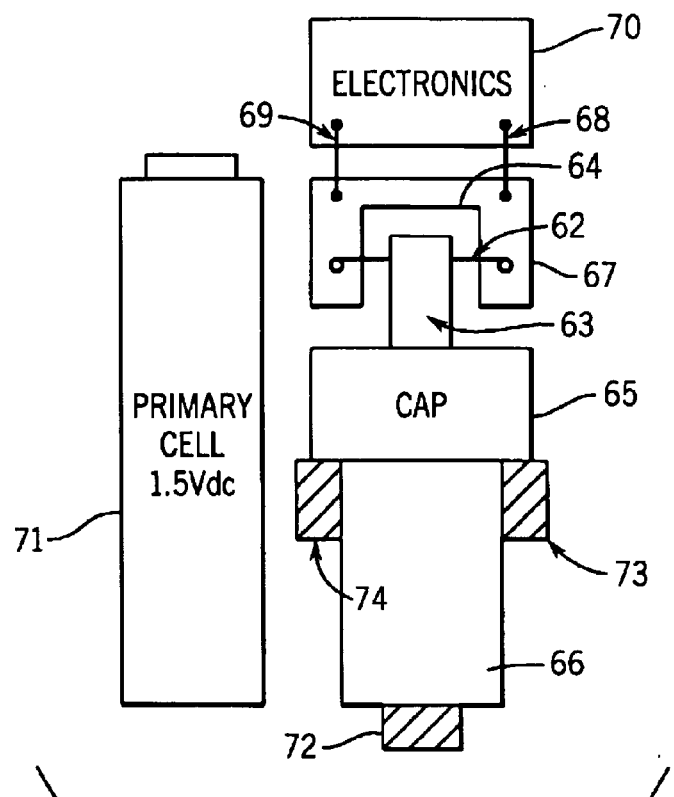
Figure 19A:
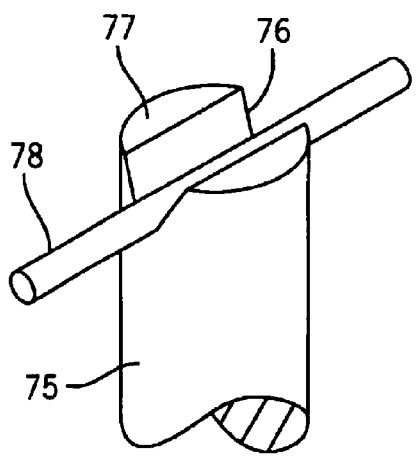
Figure 19B:
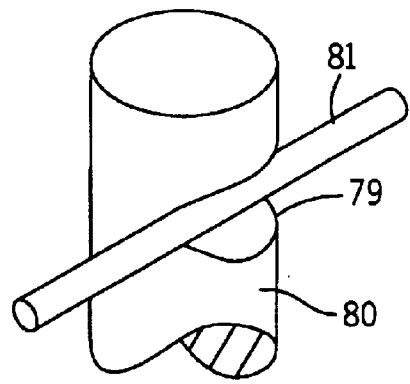
Figure 20:
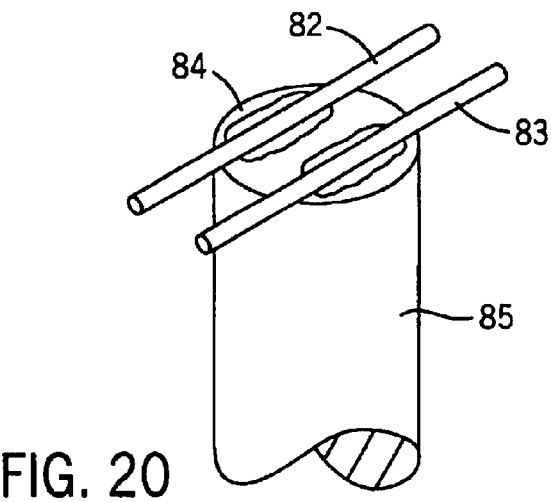
Figure 21A:
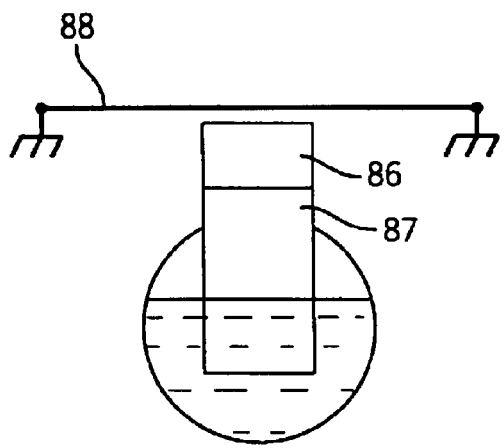
Figure 21B:
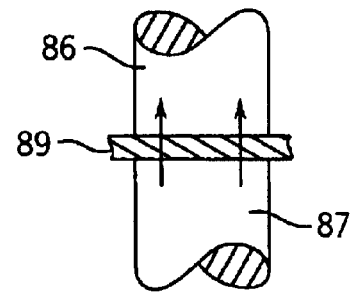
Figure 22:
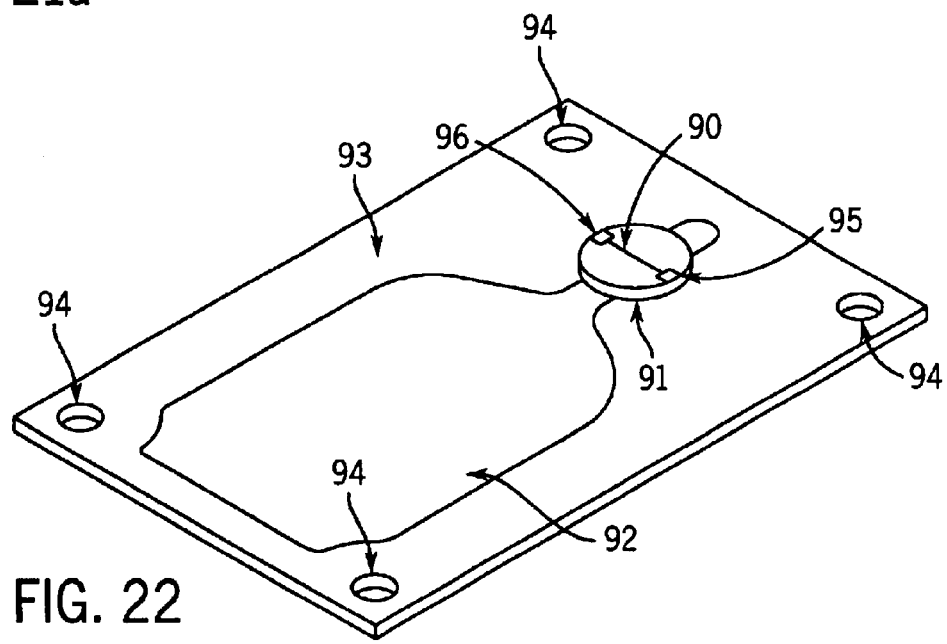
Figure 23:
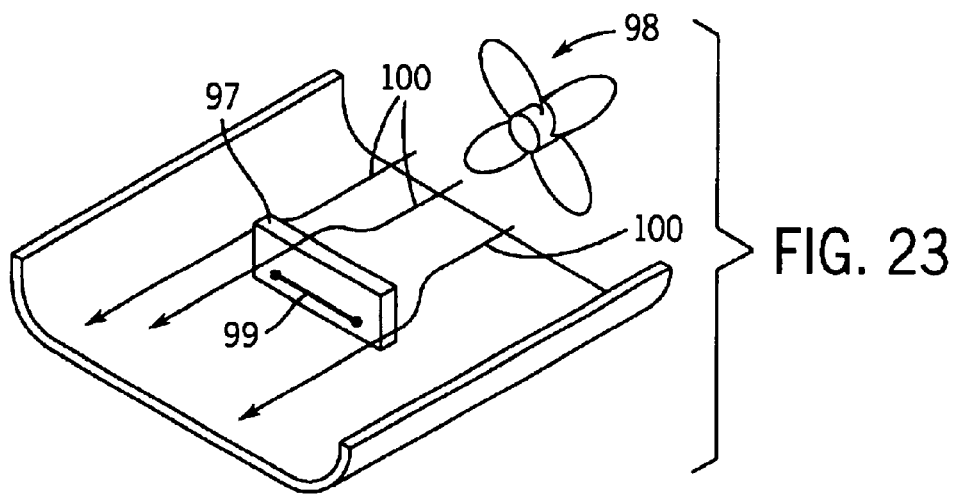
Figure 24:
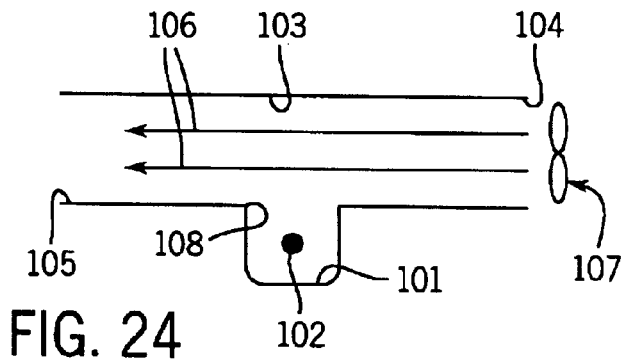
Figure 25:
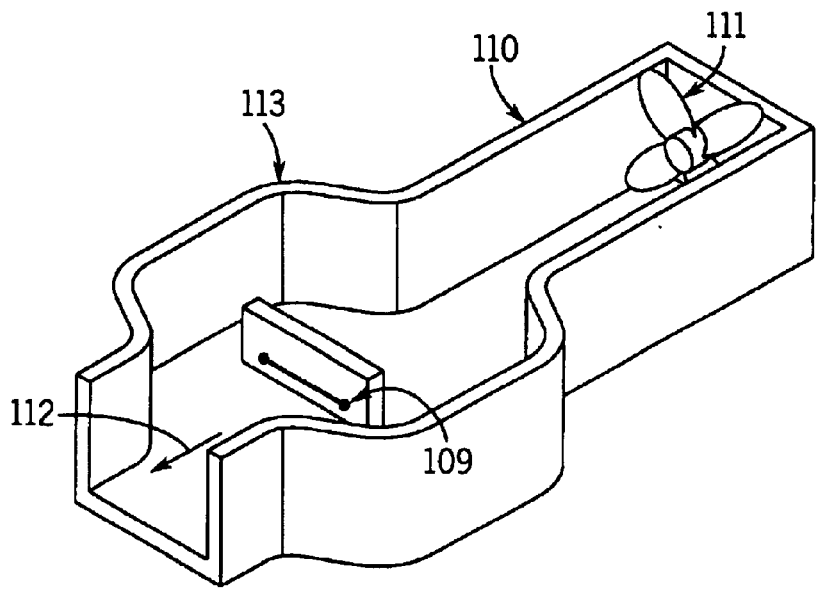
Figure 26:
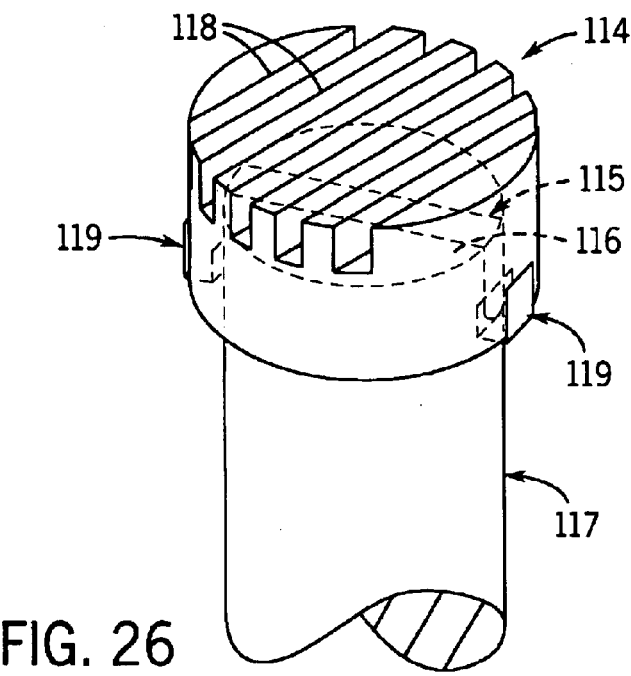
Figure 27:
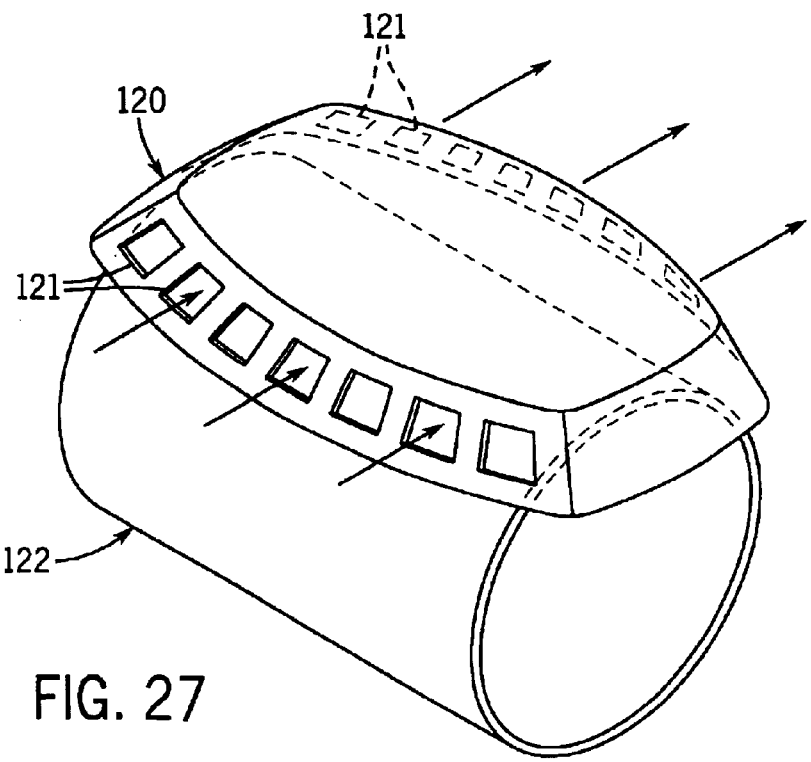

FIG. 11 schematically illustrates an end view of a wire heating element held in contact with the tip of a wick by a coil spring;

FIG. 12 is a top view of the embodiment of FIG. 11 with the spring not shown for clarity;

FIG. 13 is a plan view of the wire mounting used in the embodiment of FIG. 11;

FIG. 14 schematically illustrates a pair of spring fingers used to apply a spring force on the wire heating element;

FIG. 15 schematically illustrates spring force being applied by a pair of coiled sections of the wire heating element itself;

FIG. 16 schematically illustrates spring force being applied by corrugations integrally formed in the wire heating element itself;

FIG. 17 schematically illustrates spring force being applied by stretching a wire heating element;

FIG. 18 schematically illustrates a side mounting embodiment of the present invention;

FIGS. 19a and 19b illustrate the use of notches formed in a wick for receiving a wire heating element;

FIG. 20 illustrates yet another embodiment which utilizes a pair of wire heating elements;

FIGS. 21a and 21b illustrate a multi-part wick for delivering active to a wire heating element;

FIG. 22 illustrates an all-in-one refill unit for the present invention;

FIG. 23 illustrates the use of a fan and a baffle in the present invention;

FIG. 24 illustrates the use of a fan and a separate chamber for containing the wire heating element;

FIG. 25 illustrates the use of a fan and varying the cross sectional area of a housing for the wire heating element to control air movement past the wire heating element;

FIG. 26 illustrates the use of a cap covering the tip of a wire heating element; and FIG. 27 illustrates a vented housing as yet another embodiment of the present invention.

DETAILED DESCRIPTION OF THE INVENTION

Figure 1:
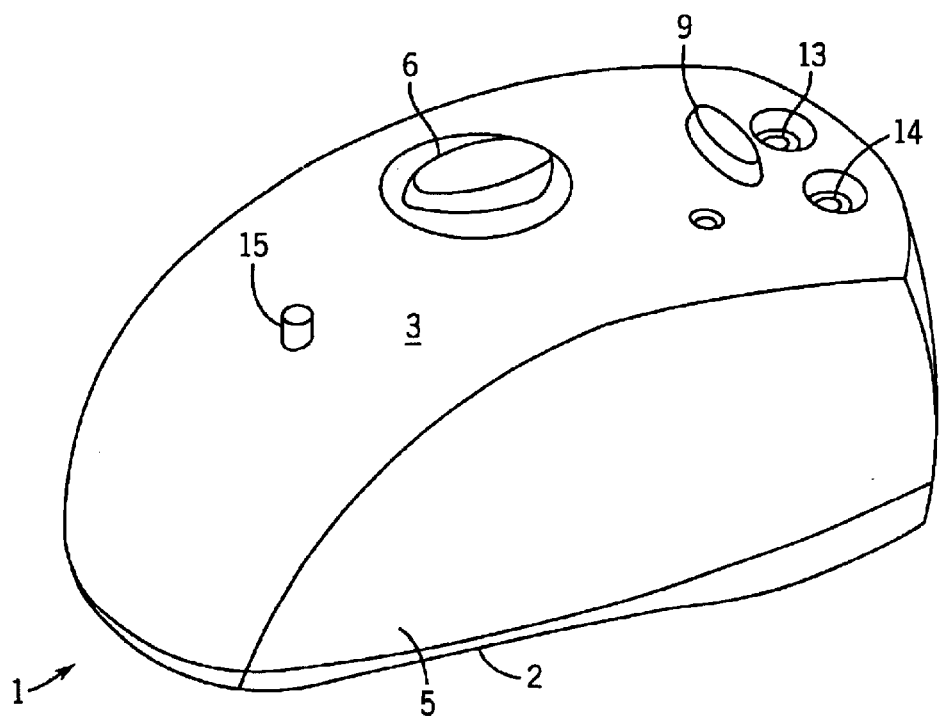
Figure 2:
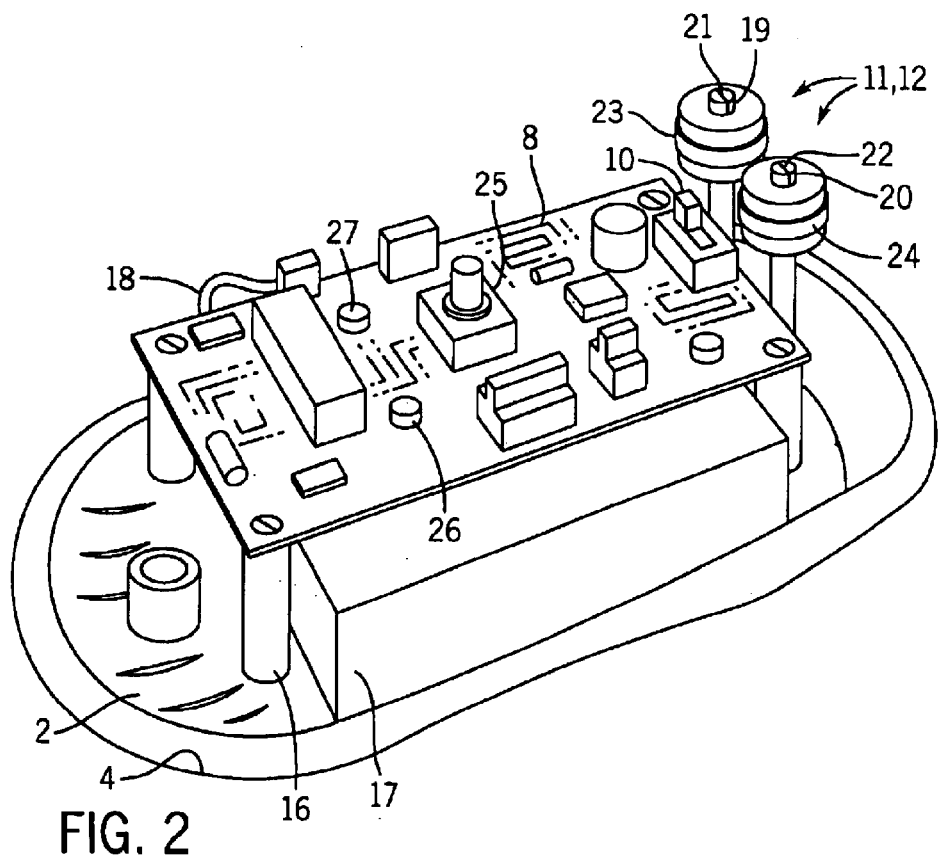

The localized and pulsed heater 1 operates as an integrated system of electrical, mechanical, and fluid systems as shown in FIGS. 1 and 2. The embodiments described herein were specifically designed for portable and semi-portable fragrancing and insecticide delivery devices. While a primary object of the invention is to provide for a portable fragrancing or insect repellent vapor-dispensing device, it should be understood that other vaporizable fluids are contemplated within the scope of the present invention, such as air fresheners, perfumes, deodorants, medicaments, and the like.

Referring now to FIGS. 1 and 2, there is illustrated one embodiment of a portable cyclic localized heater 1 constructed in accordance with the principles of the present invention. More specifically, heater 1 includes a housing which comprises a base 2 for supporting the internal components of heater 1, and a cover 3 for enclosing those components. Base 2 is in the shape of a shallow tray and includes a lip 4 at its peripheral edge which engages a corresponding lip 5 formed on cover 3 so that cover 3 may be joined with base 2 in a snap-fit arrangement. Cover 3 is thus removable so as to permit access to the interior of heater 1, if desired.

Base 2 and cover 3 can be made of any suitable, lightweight material such as a wide variety of commercially available plastics that are produced by conventional processes and known to those skilled in the art. Any plastic housing material that is selected, however, must be compatible with the particular active volative fluid that is to be vaporized. Typically, base 2 and cover 3 may be made of a commercially available polycarbonate material manufactured by known injection molding methods. Base 2 and cover 3 can thus be of any suitable dimension such that it may be readily portable whenever desired.

As shown best in FIG. 1, heater 1 includes an off duration selector knob 6 on cover 3 which is connected to an off duration potentiometer 25 mounted on circuit board 8 which in turn is supported on base 2. Knob 6 can be rotated to vary the interval between vaporization cycles. Also shown in FIG. 1 is an emanator selector knob 9 which is connected to a selector switch 10 on circuit board 8. Selector knob 9 may be slid in one direction to select a corresponding emanator 11, or in the opposite direction to select emanator 12. For example, emanator 11 may vaporize an insect repellent while emanator 12 might vaporize a fragrance so that a user can choose the particular active to be vaporized, as desired. FIG. 1 also illustrates a pair of spaced openings 13, 14 formed through cover 3 at a location which is aligned with emanators 11 and 12, respectively. Openings 13, 14 thus enable the active being vaporized to exit from heater 1 into the atmosphere. Finally, an instant action button 15 extends through cover 3, and when pushed, overrides the time delay set by the off duration knob 6 and permits a user to obtain an instant or immediate burst of active from one or both emanators 11, 12 depending upon the position of selector knob 9.

Referring now to FIG. 2, circuitboard 8 is mounted on supports 16 so as to be raised above base 2 and provide sufficient room for forming a receptacle 17 for receiving a plurality of batteries 7 (schematically shown in FIG. 3) for powering heater 1. Alternately, heater 1 may be powered by an electrical cord 18 and plug for insertion into a wall mounted electrical power outlet.

FIG. 2 also illustrates the emanators 11, 12. Each emanator 11, 12 comprises a wick 19, 20, respectively and a wire heating element 21, 22, respectively. Each wick 19, 20 has a lower end received within a reservoir 23, 24, respectively for containing a solution of an active such as an insecticide, pesticide or fragrance, and an upper end having a relatively flat tip across which wire heating elements 21, 22 respectively extend. Thus, as active is drawn upwardly by capillary action through wicks 19, 20, the solution is volatized when current is passed through wires 21, 22 resulting in heating of the solution and vaporization of the active.

Each reservoir 23, 24 is arranged to contain a volatile solution or fluid, preferably biologically active, such as an evaporable liquid insecticide or an evaporable liquid insect repellent, fragrance or the like. The reservoirs 23, 24 may be unitary with base 2 and as such may be an integral part thereof. Alternately, each reservoir 23, 24 may be separately formed and then attached to base 2 so that reservoirs 23, 24 can be removable and thereby allowing for the replacement of each reservoir after desired vaporization of the fluid contained therein. This would allow for the interchanging of a variety of like dimensioned reservoirs containing a wide variety of vaporizable liquid substances. Accordingly, the reservoirs 23, 24 can be so constructed as to be disposable and replaceable by new reservoirs containing a fresh supply of active. Also, if desired, reservoirs 23, 24 may be transparent in order to provide a user with the visual ability to determine the amount of vaporizable active or liquid remaining in the heater 1. Further, although the preferred composition is one which contains the active ingredient in a liquid solution, the composition may also be a solid, semi-solid or gel formulation under ambient conditions. In each case, the composition includes the active ingredient and a carrier for the active ingredient. The carrier may include one or more blowing agents, solvents, stabilizers, synergists, dyes and perfumes. Blowing agents include azodicarbonamide, dinitrosopentamethylenetetramine, azobisisobutyronitrile, and combinations thereof. Suitable blowing agents are disclosed in U.S. Pat. No. 4,228,124, which is hereby incorporated by reference for the purpose of disclosing blowing agents.

Solvents include alcohols such as cetyl alcohol, stearyl alcohol, and mixtures thereof.

Stabilizers (e.g., for providing stability to heat, light, and oxidation) include antioxidants such as 2,6-di-tert-butyl-4-methylphenol ("BHT"), 3-tert-butyl-4-hydroxyanisole ("BHA"), 2,2'-methylene-bis(4-ethyl-6-tert-butylphenol), 2,2'-methylene-bis-(4-methyl-6-tert-butylphenol), 4,4'-butylidene-bis(5-methyl-6-tert-butylphenol), 4,4'-methylene-bis(2-methyl-6-tert-butylphenol), 4,4'-thio-bis(3-methyl-6-tert-butylphenol), 4,4'-methylene-bis(2,6-di-tert-butylphenol), stearyl-beta(3,5-di-tert-butyl-4-hydroxyphenol)-propionate, 1,3,5-trimethyl-2,4-6-tris(3,5-di-tert-butyl-4-hydroxybenzylbenzene), 1,1,3-tris(2-methyl-4-hydroxy-5-tert-butyl)-butane, tetrakis[methylene(3,5-di-tert-butyl-4-hydroxycinnimate)]methane, dilauryl thiodipropionate, distearyl thiodipropionate, UV absorbers derived from benzophenone, triazole, and salicylate compounds, and combinations thereof. Suitable stabilizers are disclosed in U.S. Pat. No. 4,874,787 and in U.S. Pat. No. 4,515,768.

Synergists include alpha-[2-(2-butoxyethoxy)ethoxy]-4,5-methylene-dioxy-2-propyltoluene, octachlorodipropyl ether, and N-(2-ethylhexyl)-bicyclo-[2,3,2]-hept-5-en-2,3-dicarboxyimide. Suitable synergists are disclosed in U.S. Pat. Nos. 4,874,787 and U.S. Pat. No. 4,515,768.

Dyes in the composition can be used to show when the insect repellent is spent. For example, suitable dyes include 3-ethostearate of 9-ortho-carboxyphenyl-6-diethylamin-3-ethylamino-3-isoxanthene and electron-donating dyes. Dyes are disclosed in Japanese Patent Publication No's. 09-175906A and JP 07-324003A, International Patent Publication WO 96/33605 A1, and U.S. Pat. No. 5,891,811.

Perfumes can also be used in the composition. Perfumes can be used, e.g., to show when the insect repellent is spent or for aesthetic purposes. Perfumes must have similar volatility to the insect repellent and must not be attractive to insects. Examples of suitable perfumes include citronella, which can be used herein as a perfume, not an insect repellent.

Figure 3:
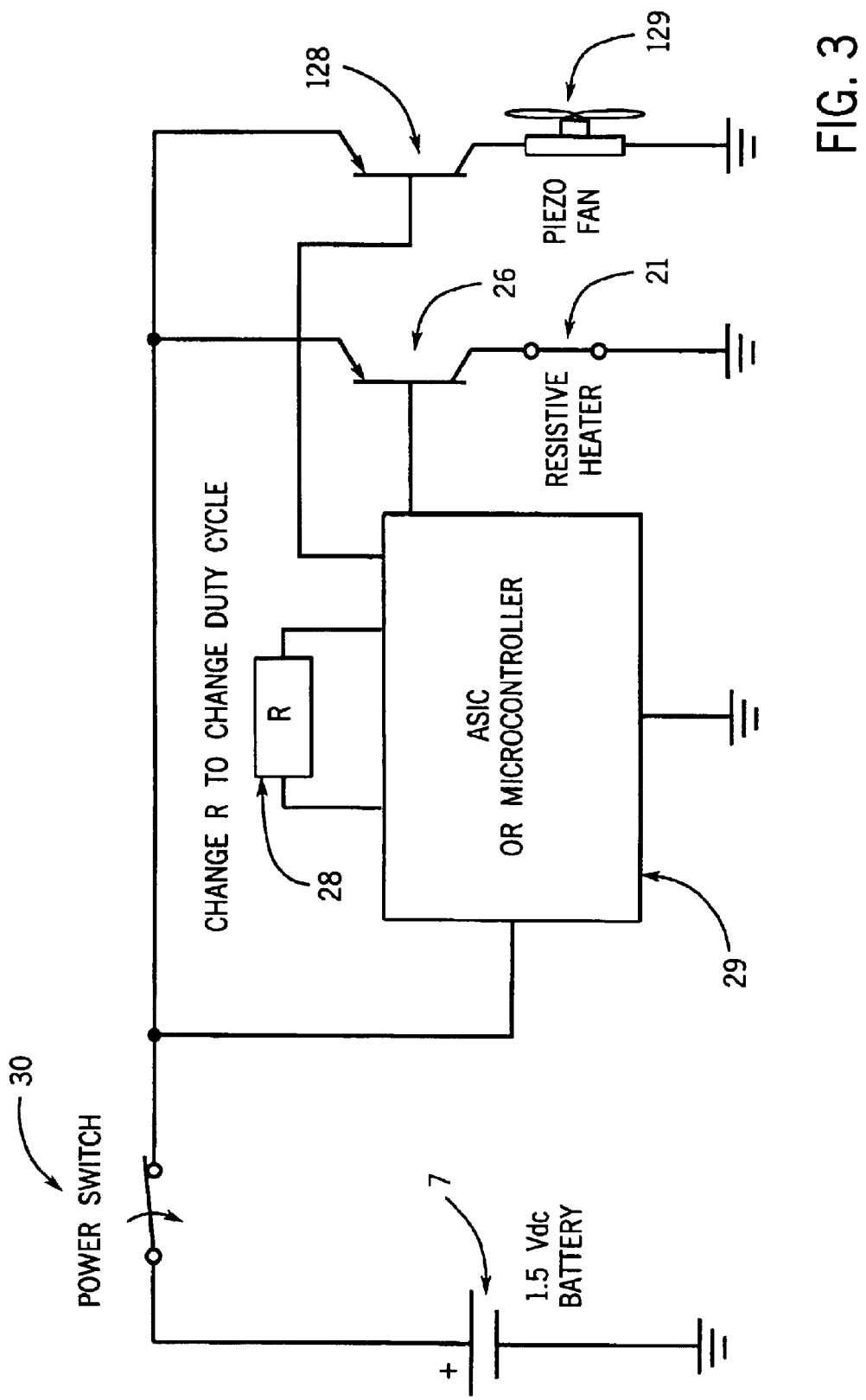

The pulsed electrical cycling of heater 1 is achieved by solid state electronic circuitry, as shown best in FIG. 3, but is not limited to the specific circuitry illustrated. The primary function for the electronics is to switch the heater 1 on and off at predetermined intervals. The ON/OFF duty cycle reduces the energy and increases battery life as compared with a device that runs continuously. The heater Control Timing can be set to operate for a predetermined specific time duration, e.g. 2 hours, 4 hours, 8 hours, etc. or can be set to turn the heater 1 on and off for predetermined time periods, e.g. on for 5 seconds and then off for five seconds as long as the Low Voltage Detector indicates a good battery(s). The duty cycle will be adjustable by changing a resistor 28 on the printed circuit board.

A secondary function for the electronics is to protect the battery(s) 7 from damage by monitoring the battery voltage and disconnecting the circuit when the voltage decreases to a set value. When the battery voltage is below a preset voltage, the electronics will enter into a Battery Low Mode. In this mode, the controls to the heater will be such that the heater is turned off. Low Battery detection is only performed during the heater off state to avoid false detection due to the current drain during the on state. The circuit will sample the battery voltage three times just before the heater on cycle and decide if the next state will be low voltage or normal (heater ON). In addition, there will be a hysteresis built into the low voltage detector circuit to remove oscillations of judgement around the low voltage level.

FIG. 3 represents a potential electronic circuit for heater 1. It is a simple, low-cost circuit and will allow the heater to be switched ON and OFF for a predetermined time (duty cycle). The ASIC, microcontroller or discrete logic component 29 incorporates a conventional Low Battery Detection circuit as is well known in this art.

The circuit of FIG. 3 will either turn the Heater ON or OFF. Depending on the heater configuration ultimately chosen, the two states of ON and OFF may not be sufficient. Take for example the situation where ON would allow too high a voltage across the heater, resulting in too high of a temperature. In that case, the ASIC, microcontroller or discrete logic component 29 will modulate the output, reducing the voltage to the heater. A pulse width modulated (PWM) method of control would be an efficient scheme for maintaining the proper voltage across the heater element 21 or 22 that is less than full ON.

The following equation is used for PWM waveforms:

$$V_{RMS} = V_{pk}\sqrt{t_{on}/T}$$

Where: $V_{pk} = V_{batt}$
$t_{ON}$ = ON time for the heater (seconds)
T = period of time for PWM output (seconds)

As can be seen from the equation, if one monitors battery voltage ($V_{pk}$) and then adjusts $t_{ON}$, one can keep $V_{RMS}$ constant.

A beneficial consequence of the use of electronics is the incorporation of a clock within the circuit to create blockout periods of the day when the device is not required and battery energy conservation can take place. As a result, once powered, heater 1 does not need to include an on/off switch such as that shown as 30 in FIG. 3 to depower the board. Specific controls of heater pulsing is provided by three subcircuits. Potentiometer 25 is adjustable to control the duration of heater off cycles from 5 seconds to 30 seconds. Potentiometer 26 allows for battery energy management with variable pulse width modulation that regulates battery use during the on cycle with an on and off subcycle to manage power needs. Other power conserving methods could be used, if desired. Potentiometer 27 is included to regulate the duration of the on cycle from 0.25 seconds to 2 seconds. Other subcircuitry can be included for motion, light, or other sensor switching such that the unit could be dormant until needed.

Power is provided by batteries 7 and could be AA, C, D, or other 3 volt battery wall power transformers. Batteries 7 may also be rechargeable. Power may also be signally or simultaneously connected to a permanent power source in a tethered or untethered manner.

The wicks 19, 20 may be constructed from natural materials, fibers, nonwovens, sintered polymers, ceramics, metal foams, open capillary tubes of ceramic, glass, or other material. A critical consideration for the selection of any of these materials is the temperature required for surface heating for the effluent being volatilized. The preferred wicking material is ceramic, in part because of its high temperature tolerance. It shares other features with some other wicks with the ability to tailor pore size to address wicking rates and fouling, it has insulative properties to further minimize heat transfer, and is readily available as a material. If the wick substrate is conductive then a dielectric material layer of a few thousandths of an inch in thickness must be placed between the electrically resistive heater and the substrate. Materials not requiring the need for dielectrics are preferred for their reduced cost, retained capillary pores for wicking, thermal stability, etc. Ceramic wicks are also preferable in that they can withstand heater deposition processing temperatures, if required. Other wick materials include wicks made from saw-dust and silica/sand mixtures that are able to withstand needed temperatures to volatize the actives.

Core to the success of this invention is the selection or creation of an appropriate electro-resistive heating element. A thermally stable material which functions as a heater when current flows from a battery is passed through it can be achieved with a wide variety of heating materials. Important to the small geometrical scale as well as the energy economy needed, heating elements from traditional materials and sources have been limited to wires, thick films, and thin films. Wire heating elements are commonly associated with alloys with trade names of Nichrome, Ohmax, Radiohm, Nirex, Nilvar, and more (Omega Engineering, Inc., Handbook and Encyclopedia, Electric Heaters, 200, pg. z-38). Pure metals that may be used, but show less resistivity and include platinum, iron, zinc, molybdenum, tungsten, and more (Omega Engineering, Inc., Handbook and Encyclopedia, Electric Heaters, 200, pg. z-38). Thin films can be derived from metallic films, oxide films, materials from nitrides, borides, carbides, stanides, and the like. Stannic oxides ($SnO_2$) or tin oxides can be deposited as a very thin film of 2 $\mu$m or less. The other metal oxides are formed as a thicker or intermediate film, but still considered as a thin films. Thick films are also possible sources of resistive heating elements. They can include electrically conductive adhesive thermosetting or thermoplastic polymeric resin pastes with silver or copper powder as the conductor. Nonresin matrices of glass and ceramics with pure metals or metal oxides such as $Al_2O_3$, BeO, Pd/Ag, SiO2, PbO, CaO, B2 O3, Na2O, K2O, MgO, and other dopants have been used as thick films. Most heating elements can be obtained in different shapes and sizes while maintaining physical properties such as electrical resistivity, density, thermal conductivity, and specific heat. These properties are determined by the constituent elements, processing methods, and post-processing techniques.

The most preferred of the above resistive heating elements is either a 49 gauge Nichrome wire or a tin oxide thin film. Important to the selection of these resistive heating elements is their effectiveness at volatilizing solutions and their energy efficiency. The gauge of the wire was selected because of its higher resistance and less energy draw to generate needed wire temperatures. Like other resistive materials, there is an issue of thinning wire diameter and the propensity for failure. The Nichrome large gauge wires are relatively fragile and are subject to mechanical failure during manufacturing, transportation, consumer handling, and use. More significantly, thermal cycling induces stresses and fatigue in the heating elements, which may result in heater failure. Undesirable oxidation of the heater material can also occur causing weakening and possible failure. FIGS. 4a through 4f illustrate various resistive wire heater designs showing a wire heating element 123a–123f touching an emanating surface 124a–124f located at the tip of a ceramic wick 125a–125f, respectively. More specifically, FIG. 4a illustrates a single straight wire heating element 123a touching a flat emanating surface 124a at the outer tip end of wick 125a. FIG. 4b illustrates a simple or single serpentine wire heating element 123b touching the flat emanating surface 124b at the tip end of ceramic wick 125b. FIG. 4c illustrates a multi-serpentine design for wire heating element 123c touching the flat emanating surface 124c at the tip end of wick 125c. FIG. 4d illustrates a wire heating element 123d that is wrapped around the circumference of the tip end of wick 125d such that the emanating surface 124d comprises the outer circumferential surface of wick 125d. FIG. 4e illustrates a pair of spaced wire heating elements 123e touching the flat emanating surface 124e at the tip end of wick 125e. It should be noted that although two wires 123e are illustrated, multiple wires could also be used, i.e. 2, 3 or more, if desired. FIG. 4f illustrates a side mounting embodiment wherein wire heating element 123f touches one side of the tip end of wick 125f such that an arcuate portion of the circumferential surface of wick 125f comprises the emanating surface 124f.

Another type of preferred resistive heating element is a vapor deposited thin film of tin oxide ($SnO_2$) or other resistive deposited films. An important consideration is the direct deposition of the oxide on the ceramic substrate that creates a mechanically robust heater that may not be as susceptible to mechanical failure. It also does not suffer, as a wire resistive heater does, from inconsistent position with respect to the wick at manufacturing and changes that occur with use. An important consideration with the use of $SnO_2$ is that its thermal expansion and that of the ceramic do not substantially differ. As a result, there is no debonding or other failures from thermal stresses that occur with pulsed or cyclic heating. Additionally the $SnO_2$ does not suffer from detrimental additional oxidation with use.

In consideration of minimizing energy use, the heating element material must have a resistivity sufficiently low to allow for rapid heating and cooling. It is therefore desirable that the heater resistance correspond to the energy density of the power source in order to minimize power consumption. Suitable heater materials of low mass, such as $SnO_2$ can be created with very low density. Not only is the composition of the resistive material important in achieving this, but also the thickness and other geometric consideration with a relationship such as R=ρ (L/(WT)). Where R is resistance of the heater, 92 is resistivity of the heater material, L is length, W is width, and T is thickness. The deposition of the thin film by atmospheric, vacuum, electro-spray, thermal, or other vapor deposition allows the resistive oxide to be applied to contoured surfaces, which also includes some internal pore surfaces.

Another advantage of a thin film heating element is that there can be an increase in surface area. This allows for increased liquid contact with the heating element to create more efficient thermal transfer and volatilization of the solution. Because of the vapor deposition method, this surface coverage can also extend into the pores of the wick, capillaries, or other structures. Yet because of the thinness of the oxide film it does not close the porous structure and does not inhibit loading performance and volatilization sites. The thin 2 μm thick films allows for the potential to layer thin films as needed to achieve desired resistivity of the heater material, in conjunction with composition, and heater design variables. Possible disadvantages of thin film resistors include: (1) some designs may actually require more energy to achieve the same temperature as a Nichrome wire; (2) some designs may become fragile especially if the substrate on which it is deposited is also thin to help minimize heat transfer; and (3) random temperature variations can occur throughout the film depending on the thickness of the film. FIGS. 5a through 5e illustrate various resistive thin film heater designs showing a thin film heating element 126a–126e located at the tip of a ceramic wick 127a–127e, respectively. More specifically, FIG. 5a illustrates a thin film heating element 126a deposited on the flat tip end of wick 127a. FIG. 5b illustrates a thin film heating element 126b deposited on flat tip end of wick 127b as well as the outer circumferential surface of wick 127b which is adjacent the flat tip end and comprising the outer edge margin of wick 127b. FIG. 5c illustrates a thin film heating element 126c deposited only around the outer circumferential surface along the edge margin and adjacent to the flat tip end of wick 127c. FIG. 5d illustrates a grid-shaped thin film heating element 126d deposited on the flat tip end of wick 127d. It should be noted that various other designs could be deposited on the flat tip end or on the circumference of wick 127d, e.g. a mesh, a spiral, a polygonal-shaped grid or some other network of spaced lines. FIG. 5e illustrates a thin film heating element 126e in the form of a thin ribbon deposited on the flat tip end of wick 127e.

As set forth above, one of the primary uses of heater 1 is for providing an insect repellant and insecticidal function. Those insecticidal or insect repellant evaporable fluids which are useful in heater 1 are limited only to the extent that such fluids are vaporizable, are of a composition which is capable of vaporization, and are registered for use with humans. The composition comprises one or more active insect repellent and one or more optional carrier ingredients. Optional carrier ingredients include blowing agents, solvents, stabilizers, synergists, dyes, and fragrances well known to those skilled in this art. Suitable insect repellents are exemplified by DEET, pyrethrins, chrysanthemic acid derivatives, and pyrethroids. Examples of some suitable pyrethroids are Allethrin, d-Allethrin, Bioallethrin, S-Bioallethrin, Empenthrin, Prallethrin, and Transfluthrin. A preferred volatile insecticidal fluid substance is 3-allyl-2-methylcyclopenta-2-ene-4-one sold under the brand name Pynamin-Forte by Sumitomo Chemical Co., Ltd. of Japan. A preferred volatile insect-repellent fluid substance is N,N-diethyl meta-toluamide (commonly known as DEET).

In additional to insect repellants, insecticides, and pesticides, the portable device of the present invention can also be utilized to evaporate other evaporable fluid substances such as evaporable fluid antiseptics, evaporable fluid agricultural fungicides, evaporable fluid plant-growth regulants, e.g. fertilizers and the like, evaporable fluid herbicides, air fresheners, perfumes, deodorants, medicaments, and the like.

A Nichrome wire will expand and contract approximately 0.001 inches during the process of heating to 160° C. and cooling. A spring mechanism is to be used to keep each Nichrome wire in constant tension against its corresponding wick. However, too much force on the wire will result in permanent deformation (stretching) of the wire or even breakage. The yield strength is the amount of stress required on the wire to permanently stretch the wire. The tensile strength is the amount of stress that would break the wire. The heater assembly must be constructed such that the stresses on the wire do not exceed one-half the yield strength. The yield and tensile strength for a 35 AWG Nichrome wire is typically 550 MPa (megapascal) and 880 MPa respectively. Therefore, ≦300 MPa of stress would be a likely target for the spring mechanism.

FIGS. 11–13 schematically illustrate one embodiment of an electro resistive wire heating element or filament 32 being held in contact with the flat tip end 33 of a wick 34. The opposite end of wick 34 is in communication with a composition containing an active ingredient within reservoir or vial 35. A cup 36 having a central opening (not shown) is used to support wick 34 in an upright position, and a seal between this opening and wick 34 prevents excessive evaporation and spillage of the composition within vial 35.

As shown best in FIG. 13, wire heating element 32 is mounted on a bowtie shaped plate 37 which includes a central annular member 38 and oppositely extending triangular shaped wing members 39 and 40. Central member 38 has an opening therein that has a diameter substantially the same as the diameter of wick 34. Wire 32 is disposed across opening 41 and has opposite ends affixed to plate 37 by rivets 41 and 42 which in turn are electrically connected to a battery 7 by wires 43 and 44 respectively.

Plate 37 and wire heating element 32 are captured within a cylindrical spring housing 45 in such a manner that plate 37 freely slides vertically therein, i.e., is free-floating in housing 45. Housing 45 includes an inwardly projecting annular lip 46 at its upper end that provides an annular lower surface 47. One end of a coil spring 48 bears against surface 47 and the other end of spring 48 bears against plate 37 so as to provide a downward force to maintain wire heating element 32 against the emanating surface, i.e., the flat tip end 33, of wick 34, as indicated by arrow 4.

Although a coil spring 48 is illustrated in FIG. 11, other types of springs are also contemplated for use in the present assembly. FIG. 14 schematically illustrates a floating wire heating element 50 mounted across a pair of spring fingers 51, 52 for movement in the direction of arrow 53. FIG. 15 schematically illustrates spring force being applied by a pair of coiled sections 54 and 55 integrally formed as part of a wire heating element 56. FIG. 16 schematically illustrates spring force being applied by corrugations 57 integrally formed as a part of a wire heating element 58. FIG. 17 schematically illustrates spring force being applied by stretching a wire heating element 59. In this embodiment, wick 60 is shouldered against the underside of plate 61 so that the flat tip end thereof projects through the central opening therein to stretch wire element 59 upwardly which provides a downward force against wick 60.

FIG. 18 schematically illustrates a side mounting embodiment for the present invention wherein a wire heating element 62 is mounted against the side of a wick 63 at a location beneath the flat tip end 64 thereof and above cap 65 of vial or reservoir 66. Wire 62 is affixed to a U-shaped plate 67 and extends across the opening formed by the U to engage or bear against the side of wick 63. A pair of spaced apart conductors 68 and 69 provide an electrical connection to the electronic circuitry schematically illustrated by 70 and battery 71. Conductors 68 and 69 are preferably composed of spring steel so as to inherently function as a spring to provide a force to maintain the wire heating element 62 in contact with the emanating surface, i.e., the side of wick 63.

FIG. 18 also illustrates a holder for removably mounting reservoir 66, cap 65 and wick 63 (comprising one embodiment of a refill assembly) to the apparatus. The holder comprises a base member 72 for supporting the underside of reservoir 66 and a pair of opposing spring finger members 73 and 74 that grab opposite sides of reservoir 66. Finger members 73 and 74 thus provide a snap-fit assembly for removably mounting reservoir 66, cap 65 and wick 63.

FIG. 19a illustrates that a wick 75 can have a notch 76 formed in its flat tip end 77 to receive a wire heating element 78. Notch 76 holds the wire heating element 78 in proper position and also increases the wetting effect at the wire heating element 78. FIG. 19b illustrates a notch 79 formed in the side of a wick 80 to receive a wire heating element 81 for the same reasons noted for FIG. 19a.

FIG. 20 illustrates yet another embodiment wherein two spaced apart wire heating elements 82 and 83 contact the flat tip end 84 of a wick 85. Multiple wire heating elements might be used if desired to volatize more effectively, to volatize at a higher rate, or as a redundant system.

FIG. 21a illustrates a multi-part delivery system wherein the device includes a two-piece (or more) wick comprised of a permanent wick portion 86 and a refill wick portion 87. The permanent wick portion 86 and a wire heating element 88 would be affixed or attached to the device so as to be non-removable while the refill wick portion 87 would be part of a refill assembly which is removable and replaceable by a user. In the case of refills, a user interacts with the device and thus it may be beneficial to isolate the heater element 88 from user interaction, thereby preventing damage to the heater, maintaining the relationship of heater-to-wick, preventing contact with a hot surface, and allowing use of a less expensive low-temperature refill wick (permanent wick portion 86 would be high-temp).

FIG. 21b illustrates that when using a two-piece, or multiple-piece wick a coupling medium 89 may need to be disposed along the interface and between portions 86 and 87 to enhance fluid transfer between the refill wick portion 87 and the permanent wick portion 86. Examples of coupling medium 89 include felt type materials, cotton, absorbent paper (e.g. filter paper) and woven fabrics. Coupling medium 89 could be affixed to either refill wick portion 87 or permanent wick portion 86.

FIG. 22 illustrates an "all-in-one" refill assembly or unit comprised of a wire heating element 90, a wick 91 and a reservoir 92 of active solution. Reservoir 92 can be formed integrally as part of a laminated plastic film package 93. The outer edges of the lamination 93 may contain holes 94, or any other desired and convenient means, for aligning the all-in-one refill unit in the device.

Contacts 95 and 96 provide an electrical connection for wire heating element 90 to a battery or other source of power via electronic circuitry (not shown). There are advantages to an all-in-one refill unit where a simple replacement assembly provides a new heater, a new delivery system (wick), and the refill active solution all at once. This method reduces the life expectancy required of the components, and eliminates the need for expensive robust hardware.

To conserve energy, it is desirable to minimize the air velocity in contact with the heater element. This is because the moving air cools the heater element and takes the heat away, and as a result more power must be supplied to the heater element to maintain a desired temp. However, one also would benefit from evacuating the air inside the housing rapidly, to reduce the active concentration surrounding the pinpoint heater because a lower concentration allows easier volatilizing. Therefore, it is desirable to move air inside the housing, but utilize an air regulation means to reduce its velocity across the heater element. FIGS. 23–26 illustrate several different methods of accomplishing this goal when used in combination with a fan while FIG. 27 illustrates another arrangement without a fan.

FIG. 23 illustrates the use of a baffle 97 as the air regulation means. Baffle 97 is disposed between a fan 98 and a wire heater element 99 in the path of the air currents 100 created by fan 98 to prevent direct contact of the air currents 100 with the wire heater element 99.

FIG. 24 illustrates the provision of a chamber 101 to receive a wire heater element 102 below (or above) a passageway 103 as the air regulation means. In FIG. 24, passageway 103 includes an air inlet 104 and an air outlet 105 formed adjacent to chamber 101 and through which air currents 106 from a fan 107 move. Passageway 103 communicates via an opening 108 with chamber 101 so that as air currents 106 flow past opening 108 active vaporized by heater element 102 is drawn into passageway 103 to flow downstream and exit the device via air outlet 105.

FIG. 25 illustrates varying the cross sectional area of a housing containing a wire heater element 109 as the air regulation means. FIG. 25 illustrates a passageway 110 formed downstream of a fan 111 through which air currents 112 move. Passageway 110 has a defined cross sectional area and opens into a larger chamber 113 having a greater cross sectional area than passageway 110 which contains wire heater element 109 therein. As a result, the velocity of the air currents 112 passing through chamber 113 and thus over wire heater element 109 is reduced as compared to the velocity of the air currents in passageway 110.

FIG. 26 illustrates an embodiment wherein the air regulation means comprises a cap 114 covering a wire heater element 115 located in contact with a flat tip end 116 of a wick 117. The cap 114 acts in a manner similar to baffle 97 in FIG. 23 to prevent direct contact of air from a fan (not shown) on wire heater element 115. In this embodiment, cap 114 also includes a plurality of slots 118 formed therein to allow active volatized by wire heater element 115 to escape the interior thereof. Cap 114 may be held on wick 117 by one or more spring clips 119 which provides a snap-fit retainer for cap 114.

FIG. 27 illustrates yet another embodiment wherein a vented housing 120 is used as the air regulation means. In FIG. 27, housing 120 includes a plurality of spaced openings 121 formed therein so that movement of ambient air therethrough will expel volatized active from the interior of housing 120. Alternatively, housing 120 may be attached via a wrist-band 122 to a user so that as a user swings or moves his or her arm, air moves through openings 121 to expel volatized active.

It should be noted that all of the embodiments illustrated and described herein may be attached to and be wearable by a user so that the device is portable and wearable. In addition to wrist band 122 noted above, other attachment means could include various clips, pins, adhesives, hook and loop fasteners, magnets, ties, necklaces, straps, bands and buckles, as is well known in the art.

It should also be noted that various types of fans can be incorporated into the device to enhance efficacy by distributing the volatized active and moving it away from the wick. For example, in addition to a conventional fan that utilizes a motor driven rotating blade, one could also use a piezo flapper device. The piezo flapper comprises a piezo device that vibrates, causing an attached material to vibrate and move air (low CFM). Alternatively, a conventional fan can be used to provide higher air velocity, as measured using cubic feet per minute (CFM). A piezo flapper uses a piezo ceramic disc or film material attached to a rectangular "flapper". The piezo vibrates at a low frequency (typically 100 hz) when excited with the proper voltage. The vibration is mechanically transferred to the flapper creating a fan that moves air. Key benefits of piezo flappers are the low energy required to activate the device, small size and high reliability. Such fans are available under the trade names Piezoelectric Bender, Piezoelectric Flapper, or Piezoelectric Chopper from companies such as Piezo Systems, Physik Instrumente GmbH & Co., and East Electronics. FIG. 3 illustrates an electronic circuit that incorporates a subcircuit including a potentiometer 128 for controlling a piezo fan 129.

EXAMPLES

Figure 6:
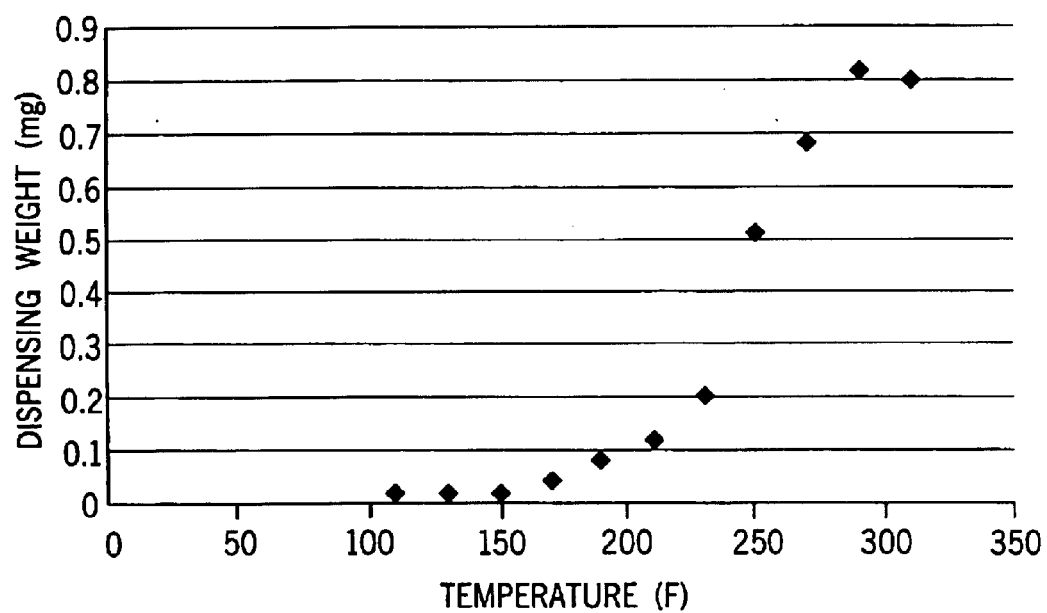
FIG. 6 is a graph illustrating the metering capability of the heater with a fragrance.

FIG. 6 is a graph that illustrates the ability of localized and cyclic heating used in heater 1 to meter the release of fragrance. This method of dispensing provides for increased control and flexibility. Current heated systems create an equilibrium release between temperature, surface area, and effluent physical properties. By controlling the amount of heat or more directly the magnitude of temperature reached, the on-time duration, and the frequency of the cycle this heating method can provide a wide range of effluent release, as shown. This experiment was conducted as shown in Table 1 with a 15 G NiCr wire resistive heating element.

TABLE 1

| Temp +/−5 (F.) | Weight per Dispensings (µg) | Weight Change (g) | Weight Initial (g) | Weight Final (g) | Dispensings (or minutes) | Dispensing Cycle (min) |
|---|---|---|---|---|---|---|
| 110 | 18.18 | 0.00020 | 14.0901 | 14.0899 | 11 | 1 |
| 130 | 20.00 | 0.00020 | 14.0894 | 14.0892 | 10 | 1 |
| 150 | 20.00 | 0.00020 | 14.0887 | 14.0885 | 10 | 1 |
| 170 | 40.00 | 0.00040 | 14.0882 | 14.0878 | 10 | 1 |
| 190 | 81.82 | 0.00090 | 14.0173 | 14.0164 | 11 | 1 |
| 210 | 120.00 | 0.00120 | 14.0853 | 14.0841 | 10 | 1 |
| 230 | 200.00 | 0.00200 | 14.0830 | 14.0810 | 10 | 1 |
| 250 | 510.00 | 0.00510 | 14.0751 | 14.0700 | 10 | 1 |
| 270 | 680.00 | 0.00680 | 14.0303 | 14.0235 | 10 | 1 |
| 290 | 815.38 | 0.01060 | 14.0098 | 13.9992 | 13 | 1 |
| 310 | 800.00 | 0.00880 | 13.9033 | 13.8945 | 11 | 1 |

Current from wall power was passed through the wire for one minute and then turned off. The amperes were controlled such that the maximum temperature achieved was that shown. Increasing the current increased the temperature and subsequently increased the weight loss per cycle. Ten to thirteen cycles were performed to obtain the average weight loss. The inflection in the profile indicates that there are temperatures that volatilize fragrance at a rate faster than fragrance can feed the heat zone during the on-cycle for volatilization. As a result, the weight loss per dispensing begins to fall with greater temperatures until a plateau occurs. During the off-cycle there is time for the emanator to recharge for another heat cycle.

Figure 7:
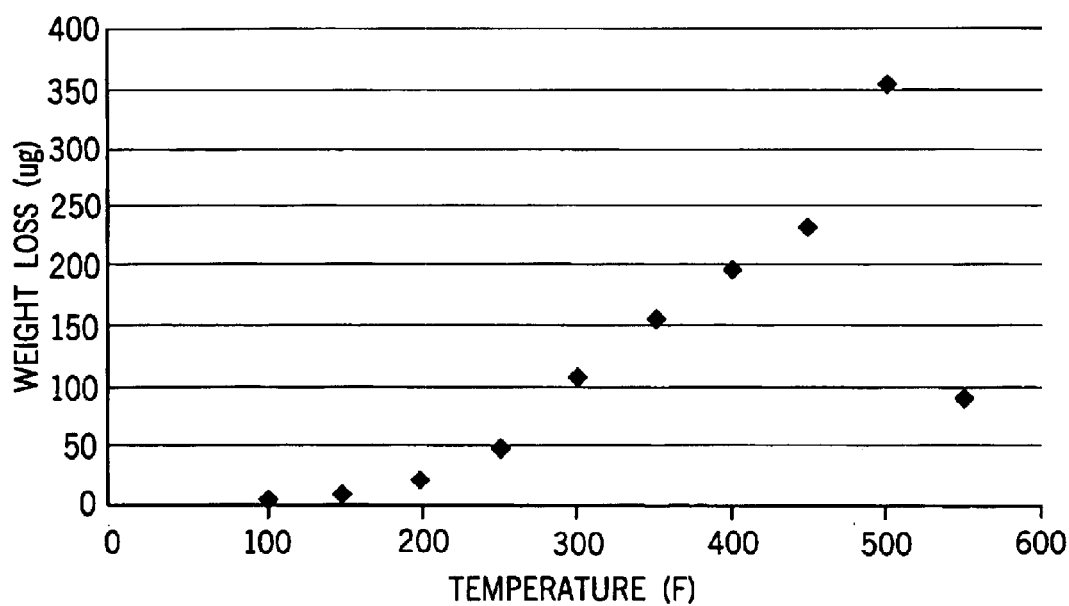
FIG. 7 is a graph illustrating the metering capability of the heater with an insecticide.

FIG. 7 is an example of the control of an insecticide by a similar experimental protocol as that described for FIG. 6. This experiment was conducted as shown in Table 2 also with a 15 G NiCr wire resistive heating element.

TABLE 2

| Temp +/−5 (F.) | Weight per Dispensings (µg) | Weight Change (g) | Initial (g) | Final (g) | Dispensings (or minutes) | Dispensing Cycle (min) |
|---|---|---|---|---|---|---|
| 100 | 3.18 | 0.0005 | 8.8945 | 8.8940 | 157 | 1 |
| 150 | 7.58 | 0.0005 | 9.0076 | 9.0071 | 66 | 1 |
| 200 | 18.48 | 0.0017 | 8.8962 | 8.8945 | 92 | 1 |
| 250 | 46.34 | 0.0038 | 9.0010 | 8.9972 | 82 | 1 |
| 300 | 109.84 | 0.0067 | 8.9972 | 8.9905 | 61 | 1 |
| 350 | 154.41 | 0.0105 | 8.9905 | 8.9800 | 68 | 1 |
| 400 | 195.96 | 0.0158 | 8.9800 | 8.9642 | 81 | 1 |
| 450 | 231.37 | 0.0118 | 8.9642 | 8.9524 | 51 | 1 |
| 500 | 352.85 | 0.0434 | 8.8940 | 8.8506 | 123 | 1 |
| 550 | 90.54 | 0.0067 | 8.9379 | 8.9312 | 74 | 1 |

The insecticides showed a similar rate limiting behavior as that with fragrances with increasing temperature.

Figure 8:
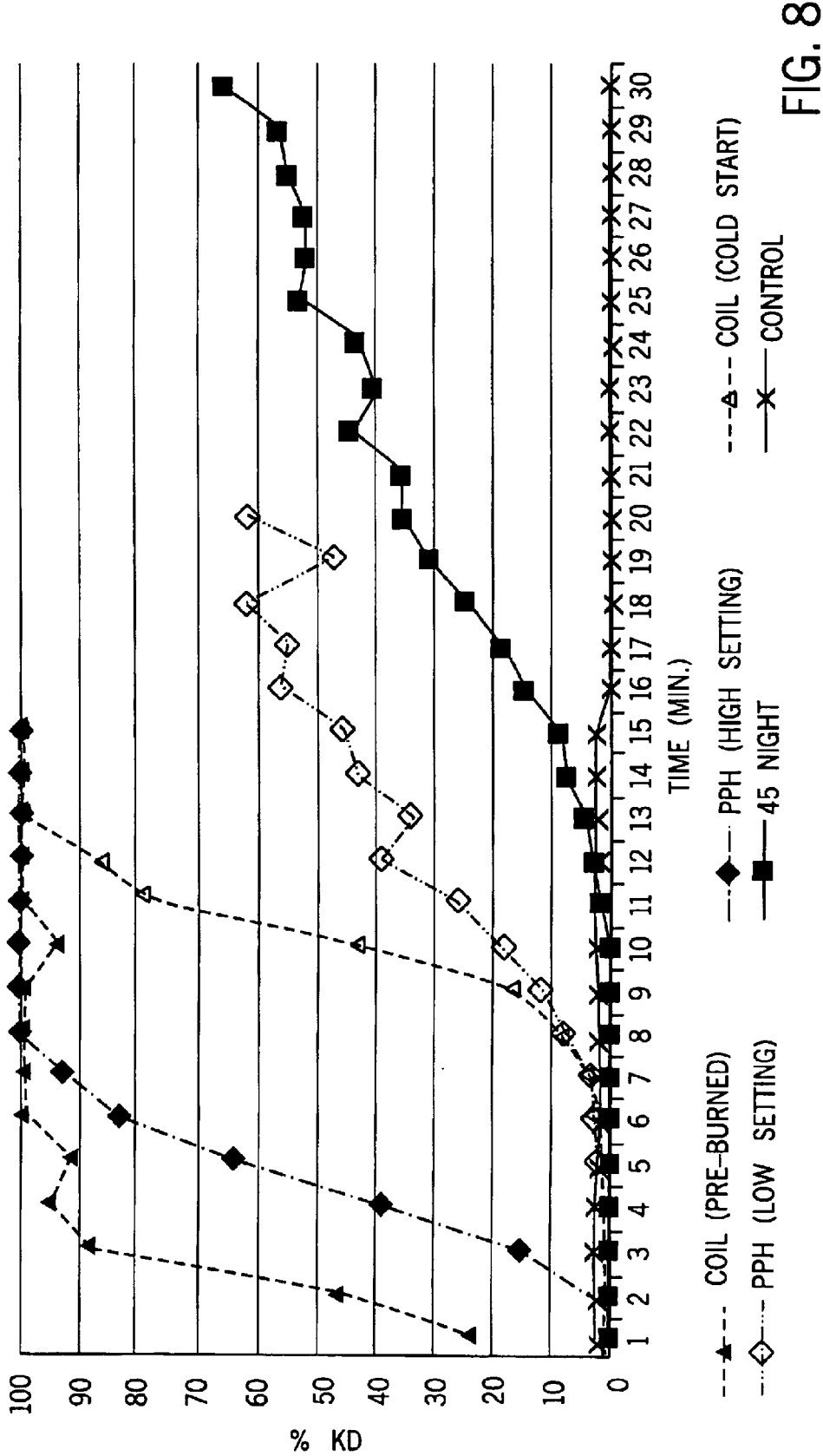
FIG. 8 is a graph illustrating the efficacy of the heater for knockdown (kill) of Aedes aegypti female mosquitoes compared to controls and a currently marketed product using a NiCr resistive wire and wall power device.

FIG. 8 represents a bioefficacy example where the same localized heating and cyclic control device used as in FIG. 7. FIG. 8 represents the adjustable performance of localized and cyclic heating against experimental controls and marketed products. Data was gathered by preparing 6.12 m$^2$ enclosed chamber with ventilation control. The chamber was cleaned with soap and water for any residual insecticide from previous tests and ventilation stopped. 100 female Aedes Aegypti mosquitoes were released in the chamber and observed for the number of mosquitoes that fell unresponsive over the course of time. FIG. 8 indicates that no mosquitoes were lost during the control experiment. The performance standard for mosquito kill or knockdown is that of the pre-burned coil. This occurs by burning a standard coil treated with an insecticide solution. Upon burning the insecticide is released and fills the chamber. A sample of 100 mosquitoes is released in this treated chamber and observed for knockdown over time. It is observed that 90% of the insects are killed with about three minutes of exposure and the remainder within the next few minutes. The "45-Night" designation represents a currently marketed product in a common form, which provides nighttime protection for 45 nights. In this and all remaining experiments in this example the chambers were prepared to control standards, the mosquitoes released and then the insecticide product released by the various devices or methods. These experiments required the device to treat the room and begin causing insect knockdown. The 45 night product showed a twelve minute lag to first efficacy. The coil from a cold start showed a seven minute lag with steeper effect against the mosquitoes. PPH represents the localized and cyclic heater and shows that it can be operated with adjustable temperature magnitude, on-time duration, and frequency to have very fast two minute onset and steep bioefficacy slope for such reasons as initial space treatment and then can be adjusted for slower onset at seven minutes and shallower slope which may represent a maintenance treatment, adjustment for smaller space, or for personal preference.

Table 3 shows an important additional conclusion from this example is the observation that the insecticide active was not destroyed by the intensive localized heating. It has been shown that the amount of active released is that which is theoretically needed for knockdown. Such theoretical values have been shown experimentally and correspond to the performance of this technology. This indicating that there is limited destruction of the chemical entity through localized cyclic heating.

TABLE 3

Active Delivered:

| Wt. Of Formula Used (g) | | Theoretical Air Concentration | | |
|---|---|---|---|---|
| | Test 1 | Test 2 | | Test 1 | Test 2 |
| Before | 10.3947 | 10.3938 | Volume (L) | 420 | 6120 |
| After | 10.3938 | 10.3917 | ug Al | 27 | 63 |
| Total used | 0.0009 | 0.0021 | ug/L | 0.0643 | 0.0103 |
| ug Al used | 27 | 63 | | | |

Test 1:
Test: 0.42 M3 chamber.
Insect: *A. aegypti*.
Formula: Raid Electric 45 night
3% EBT, 1% BHT, 96% Isopar V
Heater cycle time: 1:03 min.

| Dispensing No. | Temp. (C.) | Time (Min) | KD (#) | Total No. | KD (%) |
|---|---|---|---|---|---|
| 1 | 116 | 1 | 0 | 9 | 0 |
| 2 | 119 | 2 | 0 | 9 | 0 |
| 3 | 121 | 3 | 0 | 9 | 0 |
| 4 | 118 | 4 | 1 | 9 | 11 |
| 5 | 120 | 5 | 1 | 9 | 11 |
| 6 | 115 | 6 | 1 | 9 | 11 |
| 7 | 116 | 7 | 3 | 9 | 33 |
| 8 | 116 | 8 | 7 | 9 | 78 |
| 9 | 118 | 9 | 8 | 9 | 89 |
| 10 | 119 | 10 | 8 | 9 | 89 |
| 11 | 119 | 11 | 8 | 9 | 89 |
| 12 | 120 | 12 | 9 | 9 | 100 |

Similarly, by the use of fragrance and human panelist trained in fragrance hedonics, it has been qualitatively shown that the quality of a fragrance is also not degraded with localized cyclic heating. The burst of high temperature heating preferentially facilitates volatilization rather than degradation.

Figure 9:
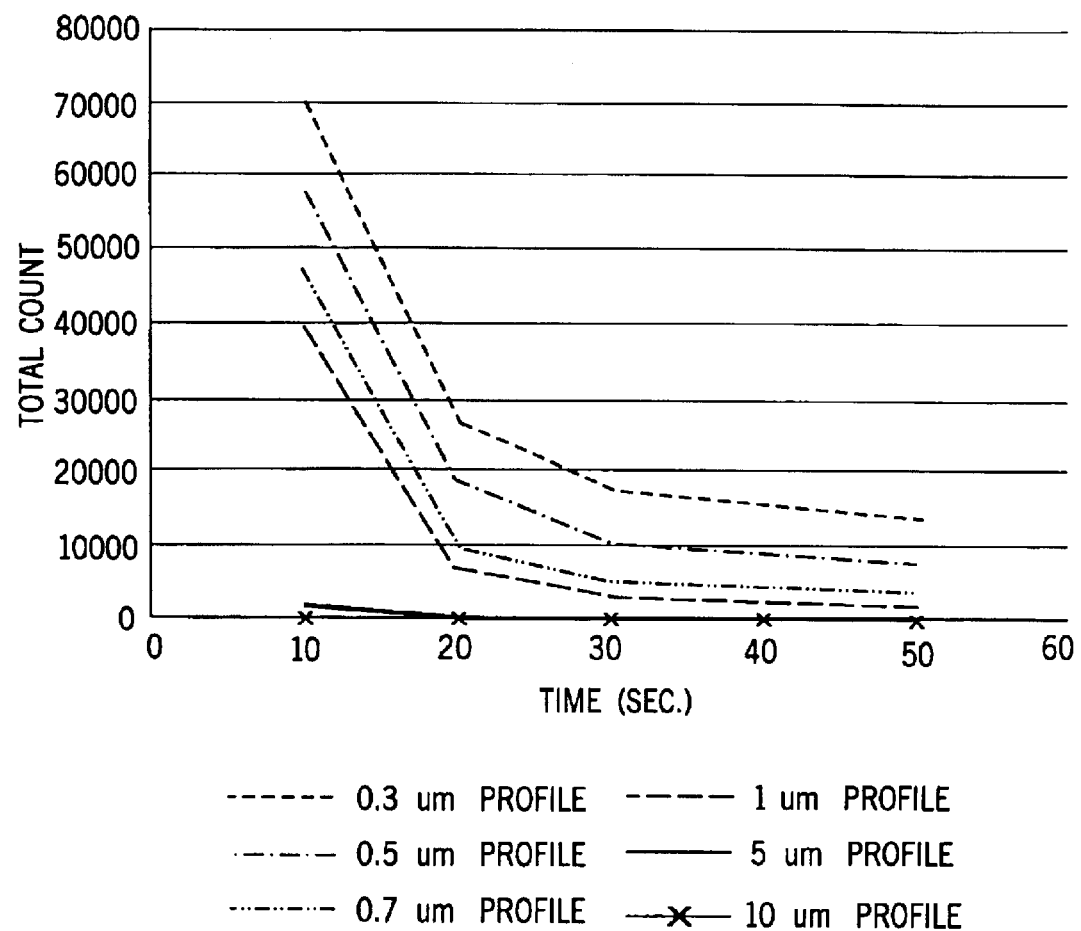
FIG. 9 is a graph illustrating the particle size generated by the heater that facilitates rapid revaporization and continued loft without fallout.
Figure 10:
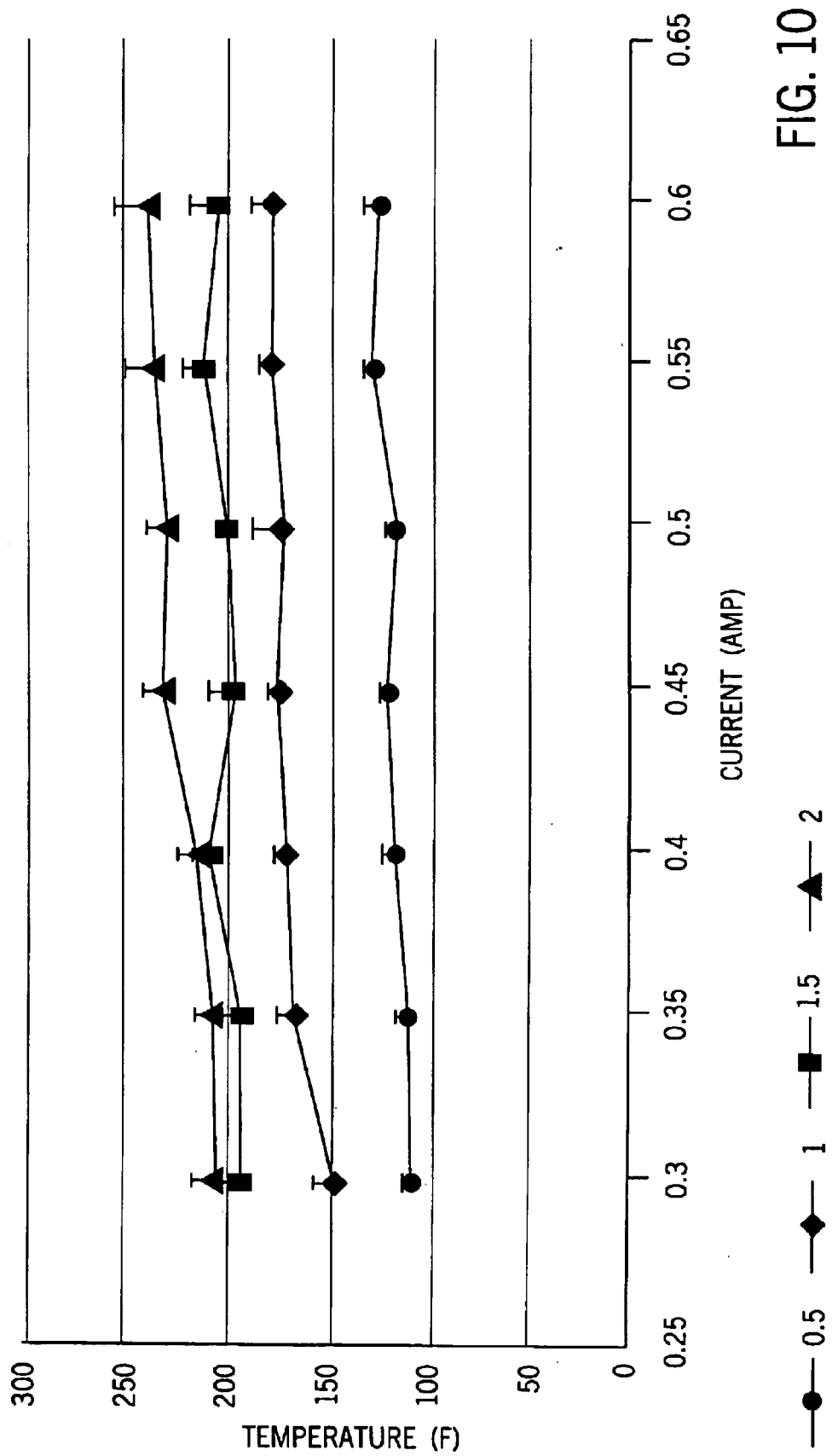
FIG. 10 is a graph illustrating a thin film resistive heater temperature responsiveness after 0.5 to 2 seconds of current.

FIG. 9 and Table 4 illustrate the favorable particle sizes created by the operation of the localized and cyclic heating of heater 1.

TABLE 4

|  | 10 | 20 | 30 | 40 | 50 |
|---|---|---|---|---|---|
| 0.3 um Profile | 69269.38 | 26828 | 17878.5 | 15459.63 | 14119 |
| 0.5 um Profile | 57631.25 | 18322.38 | 10794.13 | 8980.25 | 7921 |
| 0.7 um Profile | 47058.5 | 10181.75 | 5176.75 | 4096.875 | 3425.875 |
| 1 um Profile | 39238 | 6952.125 | 3285.375 | 2535.125 | 2073.75 |
| 5 um Profile | 730.625 | 21.5 | 12.375 | 10.625 | 9.75 |
| 10 um Profile | 5 | 0.25 | 0.25 | 0.25 | 0.25 |

The mechanism of molecular volatilization and detection of particles results form the condensation of the vapor within the vicinity of the emanator. The size and energy (retained heat) of these particles is important in their post condensation behavior. Particles that are too large suffer from lack of time aloft and lack of surface area. Large particles of 2–3 μm and particularly above 10 μm in diameter or more are affected by gravity and will fall out of suspension in the air near the emanator. Because of the lack of loft the particles are not able to drift to lower concentrated areas where they can revaporize. Contributing to the difficulty to revolatilize is the reduced surface area per volume of the larger particles, which limits the amount of surface available for volatilizations. Just the opposite is available from the localize cyclic heating method of the present invention. These particles have reduced diameter below 1 μm, which are too small to settle out from gravitational forces, are too small to deposit in human respiratory system, and have large surface to volume ratios such that revolatilization is quickly promoted. The particles from the localized cyclic heat source of heater 1 efficiently disperse and remain dispersed in air.

FIG. 10 and Table 5 demonstrate the variable temperatures that are achievable with a single thin film oxide heater with variable current input.

TABLE 5

| Amp | 0.5 Temp (F.) | 1 Temp (F.) | 1.5 Temp (F.) | 2 Temp (F.) |
|---|---|---|---|---|
| 0.3 | 119.72 | 103.30 | 85.66 | 63.14 |
| 0.35 | 130.19 | 111.89 | 92.43 | 69.01 |
| 0.4 | 126.72 | 106.92 | 89.96 | 67.46 |
| 0.45 | 0.45 | 0.45 | 0.45 | 0.45 |
| 0.5 | 0.50 | 0.50 | 0.50 | 0.50 |
| 0.55 | 120.75 | 106.80 | 88.93 | 65.50 |
| 0.6 | 128.90 | 111.11 | 91.01 | 67.34 |

This example illustrates one composition with surface temperatures can vary over broad ranges. It also represents that final temperatures are largely achieved within the first half second of current application. There is little temperature, change between one-half second and two seconds. This example confirms the rapid heating characteristics of the thin film heating element within appropriate ranges for use within the fields described by this application.

What is claimed is:

1. A portable apparatus for dispersing a volatile active into air, comprising:

a base;

a reservoir containing a composition having a volatile active;

a holder for mounting said reservoir to said base;

a wick having an emanating surface and communicating with said composition for delivering said composition to said emanating surface;

a heating element in contact with said emanating surface; and a source of power communicating with said heating element to heat said heating element and vaporize said volatile active;

wherein said holder provides a removable mounting for said reservoir;

wherein said reservoir and wick are integral with each other to provide a removable and replaceable refill assembly; and wherein said refill assembly further includes said heating element.

2. The apparatus of claim 1 wherein said volatile active is selected from the group consisting of an insect repellant, an insecticide, a pesticide, an antiseptic, a fungicide, a plant growth regulator, a herbicide, an air freshener, a perfume, a deodorant, a medicament, and mixtures thereof.

3. The apparatus of claim 1 wherein said volatile active is an insect repellant.

4. The apparatus of claim 3 wherein said insect repellant is selected from the group consisting of pyrethrins, chrysanthemic acid derivatives, pyrethroids, and mixtures thereof.

5. The apparatus of claim 4 wherein said insect repellant is a pyrethroid and is selected from the group consisting of allethrin, d-allethrin, bioallethrin, S-bioallethrin, empenthrin, prallethrin, and transfluthrin, and combinations thereof.

6. The apparatus of claim 3 wherein said insect repellant is 3-allyl-2-methylcyclopenta-2-ene-4-one.

7. The apparatus of claim 3 wherein said insect repellant is N,N-diethyl meta-toluamide.

8. The apparatus of claim 1 wherein said holder provides a snap-fit mounting for said refill assembly.

9. The apparatus of claim 1 wherein said wick is composed of a material selected from the group consisting of natural materials, fibers, nonwovens, sintered polymers, ceramics, metal foams and glass.

10. The apparatus of claim 1 wherein said heating element is an electro-resistive heating element.

11. The apparatus of claim 10 wherein said electro-resistive heating element is selected from the group consisting of a wire, a thin film and a thick film.

12. The apparatus of claim 10 wherein said electro-resistive heating element is a wire composed of nichrome.

13. The apparatus of claim 10 wherein said electro-resistive heating element is a thin film composed of tin oxide.

14. The apparatus of claim 1 wherein said composition is in the form of a liquid, solid, semi-solid or gel at ambient conditions.

15. A portable apparatus for dispersing a volatile active into air, comprising:
a base;
a reservoir containing a composition having a volatile active;
a holder for mounting said reservoir to said base;
a wick having an emanating surface and communicating with said composition for delivering said composition to said emanating surface;
a heating element in contact with said emanating surface;
a source of power communicating with said heating element to heat said heating element and vaporize said volatile active; and
a spring providing a force to maintain said wire heating element in contact with said emanating surface.

16. The apparatus of claim 15 wherein said wick includes a relatively flat tip end defining said emanating surface and said heating element contacts said flat tip end.

17. The apparatus of claim 15 wherein said wick includes opposite ends and at least one side surface between said opposite ends defining said emanating surface and said heating element contacts said side surface.

18. A portable apparatus for dispersing a volatile active into air, comprising:
a base;
a reservoir containing a composition having a volatile active;
a holder for mounting said reservoir to said base;
a wick having an emanating surface and communicating with said composition for delivering said composition to said emanating surface;
a wire heating element in contact with said emanating surface;
a spring providing a force to maintain said wire heating element in contact with said emanating surface; and
a source of power communicating with said heating element to heat said heating element and vaporize said volatile active.

19. The apparatus of claim 18 wherein said volatile active is selected from the group consisting of an insect repellant, an insecticide, a pesticide, an antiseptic, a fungicide, a plant growth regulator, a herbicide, an air freshener, a perfume, a deodorant, a medicament, and mixtures thereof.

20. The apparatus of claim 18 wherein said volatile active is an insect repellant.

21. The apparatus of claim 20 wherein said insect repellant is selected from the group consisting of pyrethrins, chrysanthemic acid derivatives, pyrethroids, and mixtures thereof.

22. The apparatus of claim 21 wherein said insect repellant is a pyrethroid and is selected from the group consisting of allethrin, d-allethrin, bioallethrin, S-bioallethrin, empenthrin, prallethrin, and transfluthrin, and combinations thereof.

23. The apparatus of claim 20 wherein said insect repellant is 3-allyl-2-methylcyclopenta-2-ene-4-one.

24. The apparatus of claim 20 wherein said insect repellant is N,N-diethyl meta-toluamide.

25. The apparatus of claim 18 wherein said holder provides a removable mounting for said reservoir.

26. The apparatus of claim 25 wherein said reservoir and wick are integral with each other to provide removable and replaceable refill assembly.

27. The apparatus of claim 26 wherein said refill assembly further includes said heating element.

28. The apparatus of claim 25 wherein said holder provides a snap-fit mounting for said refill assembly.

29. The apparatus of claim 18 wherein said wick is composed of a material selected from the group consisting of natural materials, fibers, nonwovens, sintered polymers, ceramics, metal foams and glass.

30. The apparatus of claim 18 wherein said wire heating element is composed of nichrome.

31. The apparatus of claim 18 wherein said composition is in the form of a liquid, solid, semi-solid or gel at ambient conditions.

32. The apparatus of claim 18 wherein said wick includes a relatively flat tip end defining said emanating surface and said heating element contacts said flat tip end.

33. The apparatus of claim 18 wherein said wick includes opposite ends and at least one side surface between said opposite ends defining said emanating surface and said heating element contacts said side surface.

34. A portable apparatus for dispersing a volatile active into air,
comprising:
a base;
a refill assembly comprising a reservoir containing a composition having a volatile active, a wick having an emanating surface and communicating with said composition for delivering said composition to said emanating surface, and a heating element in contact with said emanating surface;
a holder for removably mounting said refill assembly to said base;
a source of power communicating with said heating element to heat said heating element and vaporize said volatile active;
a spring providing a force to maintain said heating element in contact with said emanating surface;
a cover attachable to said base to enclose said refill assembly, holder and spring, and including at least one air inlet and one air outlet; and
a fan mounted to move a current of air from said inlet past said emanating surface to cause egress of said volatile active from said air outlet.

35. The apparatus of claim 34 wherein said volatile active is selected from the group consisting of an insect repellant, an insecticide, a pesticide, an antiseptic, a fungicide, a plant growth regulator, a herbicide, an air freshener, a perfume, a deodorant, a medicament, and mixtures thereof.

36. The apparatus of claim 34 wherein said volatile active is an insect repellant.

37. The apparatus of claim 36 wherein said insect repellant is selected from the group consisting of pyrethrins, chrysanthemic acid derivatives, pyrethroids, and mixtures thereof.

38. The apparatus of claim 37 wherein said insect repellant is a pyrethroid and is selected from the group consisting of allethrin, d-allethrin, bioallethrin, S-bioallethrin, empenthrin, prallethrin, and transfluthrin, and combinations thereof.

39. The apparatus of claim 36 wherein said insect repellant is 3-allyl-2-methylcyclopenta-2-ene-4-one.

40. The apparatus of claim 36 wherein said insect repellant is N,N-diethyl meta-toluamide.

41. The apparatus of claim 34 wherein said holder provides a removable mounting for said reservoir.

42. The apparatus of claim 41 wherein said holder provides a snap-fit mounting for said refill assembly.

43. The apparatus of claim 34 wherein said wick is composed of a material selected from the group consisting of natural materials, fibers, nonwovens, sintered polymers, ceramics, metal foams and glass.

44. The apparatus of claim 34 wherein said heating element is an electro-resistive heating element.

45. The apparatus of claim 44 wherein said electro-resistive heating element is selected from the group consisting of a wire, a thin film and a thick film.

46. The apparatus of claim 44 wherein said electro-resistive heating element is a wire composed of nichrome.

47. The apparatus of claim 44 wherein said electro-resistive heating element is a thin film composed of tin oxide.

48. The apparatus of claim 34 further including a battery housing mounted on said base, and wherein said source of power comprises at least one battery receivable in said battery housing for powering said heating element and fan.

49. The apparatus of claim 34 further including air regulation means for minimizing the velocity of said air current across said heater element.

50. The apparatus of claim 49 wherein said air regulation means includes a baffle disposed between said fan and said heater element to prevent direct contact of said air current with said heater element.

51. The apparatus of claim 49 wherein said air regulation means comprises a passageway formed adjacent to said heater element and communicating with said air inlet and said air outlet and through which said air current moves, said passageway communicating with said heater element to draw active vaporized by said heater element into said passageway as said air moves downstream therein.

52. The apparatus of claim 49 wherein said air regulation means comprises a passageway formed downstream of said fan through which said air current moves and having a first cross sectional area, and a chamber downstream of said passageway through which said air current moves and having a second cross sectional area, said second cross sectional area being greater than said first cross sectional area to thereby reduce the velocity of said air current through said chamber, and said heater element is disposed in said chamber.

53. The apparatus of claim 34 further including a non-removable permanent wick portion engageable with said wick of said refill assembly.

54. The apparatus of claim 53 further including a fluid coupling medium disposed between said permanent wick portion and said wick of said refill assembly.

55. The apparatus of claim 34 wherein said source of power includes electronic circuitry providing pulsed heating of said heating element.

* * * * *